US012760366B2

(12) United States Patent
Gudjonsson et al.

(10) Patent No.: US 12,760,366 B2
(45) Date of Patent: Oct. 13, 2026

(54) METHODS FOR DETERMINING RESPONSIVENESS TO ANTI-TUMOR NECROSIS FACTOR THERAPY IN THE TREATMENT OF PSORIASIS

(71) Applicant: THE REGENTS OF THE UNIVERSITY OF MICHIGAN, Ann Arbor, MI (US)

(72) Inventors: Johann Gudjonsson, Ann Arbor, MI (US); Lam Cheung Tsoi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1185 days.

(21) Appl. No.: 17/765,508

(22) PCT Filed: Oct. 2, 2020

(86) PCT No.: PCT/US2020/053900
§ 371 (c)(1),
(2) Date: Mar. 31, 2022

(87) PCT Pub. No.: WO2021/067667
PCT Pub. Date: Apr. 8, 2021

(65) Prior Publication Data

US 2022/0364174 A1 Nov. 17, 2022

Related U.S. Application Data

(60) Provisional application No. 62/910,871, filed on Oct. 4, 2019.

(51) Int. Cl.
*C12Q 1/6883* (2018.01)
*C12Q 1/6879* (2018.01)

(52) U.S. Cl.
CPC ......... *C12Q 1/6883* (2013.01); *C12Q 1/6879* (2013.01)

(58) Field of Classification Search
None
See application file for complete search history.

(56) References Cited

U.S. PATENT DOCUMENTS

2017/0037476 A1* 2/2017 Eyerich .............. G01N 33/6881

FOREIGN PATENT DOCUMENTS

| | | | | |
|---|---|---|---|---|
| EA | 016240 | | 3/2012 | |
| JP | 2015522260 | A | 8/2015 | |
| RU | 2012146845 | A | 5/2014 | |
| WO | WO-2005100603 | A2 | 10/2005 | |
| WO | 2009/100342 | A2 | 8/2009 | |
| WO | WO-2013188846 | A1 | 12/2013 | |
| WO | WO-2015155767 | A1 | 10/2015 | |
| WO | WO-2017093750 | A1 * | 6/2017 | ............ G16H 50/30 |

OTHER PUBLICATIONS

Cobb et al (Crit Care Med 2002 vol. 30 p. 2711) (Year: 2002).*
Anders et al., HTSeq—a Python framework to work with high-throughput sequencing data, Bioinformatics, 31(2):166-9 (2015).
Arican et al., Serum levels of TNF-alpha, IFN-gamma, IL-6, IL-8, IL-12, IL-17, and IL-18 in patients with active psoriasis and correlation with disease severity, Mediators Inflamm., 2005(5):273-9 (2005).
Armstrong et al., Standardizing training for psoriasis measures: effectiveness of an online training video on Psoriasis Area and Severity Index assessment by physician and patient raters, JAMA Dermatol., 149(5):577-82 (2013).
Aziz et al., Towards personalized medicine of colorectal cancer, Crit. Rev. Oncol. Hematol., 118:70-8 (2017).
Blauvelt et al., Certolizumab pegol for the treatment of patients with moderate-to-severe chronic plaque psoriasis: pooled analysis of week 16 data from three randomized controlled trials, J. Eur. Acad. Dermatol. Venereal., 33(3):546-552 (2019).
Bolger et al., Trimmomatic: a flexible trimmer for Illumina sequence data, Bioinformatics, 30(15):2114-20 (2014).
Caldarola et al., TNFalpha and its receptors in psoriatic skin, before and after treatment with etanercept, Int. J. Immunopathol. Pharmacol., 22(4):961-6 (2009).
Chan et al., Novel Strategies on Personalized Medicine for Breast Cancer Treatment: An Update, Int. J. Mol. Sci., 18(11):2423 (2017).
Chaudhari et al., Efficacy and safety of infliximab monotherapy for plaque-type psoriasis: a randomised trial, Lancet, 357(9271):1842-47 (2001).
Conesa et al., A survey of best practices for RNA-seq data analysis, Genome Biol., 17:13 (2016).
Conrad et al., TNF blockade induces a dysregulated type I interferon response without autoimmunity in paradoxical psoriasis, Nat. Commun., 9(1):25 (2018).
Dobin et al., STAR: ultrafast universal RNA-seq aligner, Bioinformatics, 29(1):15-21 (2013).
Dowlatshahi et al., Markers of systemic inflammation in psoriasis: a systematic review and meta-analysis, Br. J. Dermatol., 169(2):266-82 (2013).
Flamant et al., Inflammatory bowel disease: towards a personalized medicine, Therap. Adv. Gastroenterol., 11:1-15 (2018).
Foulkes et al., Genetic prediction of treatment response in psoriasis is still a work in progress, Br. J. Dermatol., 177(2):344-5 (2017).
Gisondi et al., Biologic therapies in psoriasis: a new therapeutic approach, Autoimmun Rev., 6(8):515-9 (2007).

(Continued)

*Primary Examiner* — Katherine D Salmon
(74) *Attorney, Agent, or Firm* — MARSHALL, GERSTEIN & BORUN LLP

(57) ABSTRACT

The disclosure relates to the development of methods for predicting effectiveness of an anti-TNF agent in the treatment of psoriasis. More particularly, the disclosure provides new biomarkers and combinations of biomarkers for predicting effectiveness of an anti-TNF agent in the treatment of psoriasis and subsequently treating with an anti-TNF agent if the biomarker level is indicative of effectiveness in the anti-TNF treatment of the subject.

10 Claims, 13 Drawing Sheets

(56) References Cited

OTHER PUBLICATIONS

Gordon et al., Clinical response to adalimumab treatment in patients with moderate to severe psoriasis: double-blind, randomized controlled trial and open-label extension study, J. Amer. Acad. Dermatol., 55(4):598-606 (2006).
Gudjonsson et al., Assessment of the psoriatic transcriptome in a large sample: additional regulated genes and comparisons with in vitro models, J. Invest. Dermatol., 130(7):1829-40 (2010).
Gudjonsson et al., Global gene expression analysis reveals evidence for decreased lipid biosynthesis and increased innate immunity in uninvolved psoriatic skin, J. Invest. Dermatol., 129(12):2795-804 (2009).
Horton et al., Empowering Mayo Clinic Individualized Medicine with Genomic Data Warehousing, J. Pers. Med., 7(3):7 (2017).
International Application No. PCT/US20/53900, International Search Report and Written Opinion, mailed Feb. 4, 2021.
International Application No. PCT/US20/53900, International Preliminary Report on Patentability, mailed Apr. 14, 2022.
Johansen et al., Protein expression of TNF-alpha in psoriatic skin is regulated at a posttranscriptional level by MAPK-activated protein kinase 2, J. Immunol., 176(3):1431-8 (2006).
Kavanaugh et al., Golimumab, a new human tumor necrosis factor alpha antibody, administered every four weeks as a subcutaneous injection in psoriatic arthritis: Twenty-four-week efficacy and safety results of a randomized, placebo-controlled study, Arthritis Rheum., 60(4):976-86 (2009).
Kim et al., TNF-a downregulates filaggrin and loricrin through c-Jun N-terminal kinase: role for TNF-a antagonists to improve skin barrier, J. Invest. Dermatol., 131(6):1272-9 (2011).
Kivelevitch et al., Long term efficacy and safety of etanercept in the treatment of psoriasis and psoriatic arthritis, Biologics., 8:169-82 (2014).
Koczan et al., Molecular discrimination of responders and nonresponders to anti-TNFalpha therapy in rheumatoid arthritis by etanercept, Arthritis Research And Therapy, 10(3):R50 (2008).
Krueger et al., Involved and uninvolved skin from psoriatic subjects: are they equally diseased? Assessment by skin transplanted to congenitally athymic (nude) mice, J. Clin. Invest., 68(6):1548-57 (1981).
Krueger et al., Patients with psoriasis respond to continuous open-label etanercept treatment after initial incomplete response in a randomized, placebo-controlled trial, J. Amer. Acad. Derm., 54(3 Suppl 2):S112-9 (2006).
Leonardi et al., Etanercept as monotherapy in patients with psoriasis, N. Engl. J. Med., 349(21):2014-22 (2003).
Li et al., Transcriptome analysis of psoriasis in a large case-control sample: RNA-seq provides insights into disease mechanisms, J. Invest. Dermatol., 134(7):1828-38 (2014).
Love et al., Moderated estimation of fold change and dispersion for RNA-seq data with DESeq2, Genome Biol., 15(12):550 (2014).
Paller et al., Long-term etanercept in pediatric patients with plaque psoriasis, J. Amer. Acad. Dermatol., 63(5):762-8 (2010).
Sarkar et al., Photosensitivity and type I IFN responses in cutaneous lupus are driven by epidermal-derived interferon kappa, Ann. Rheum. Dis., 77(11):1653-1664 (2018).
Tavakolpour, Towards personalized medicine for patients with autoimmune diseases: Opportunities and challenges, Immunol. Lett., 190:130-8 (2017).
Tsoi et al., Analysis of long non-coding RNAs highlights tissue-specific expression patterns and epigenetic profiles in normal and psoriatic skin, Genome Biol., 16(1):24 (2015).
Tsoi et al., Atopic Dermatitis Is an IL-13-Dominant Disease with Greater Molecular Heterogeneity Compared to Psoriasis, J. Invest. Dermatol., 139(7):1480-1489 (2019).
Tsoi et al., Identification of 15 new psoriasis susceptibility loci highlights the role of innate immunity, Nature Genetics, 44(12):1341-8 (2012).
Tsoi et al., Large scale meta-analysis characterizes genetic architecture for common psoriasis associated variants, Nat. Commun., 8:15382 (2017).
Tsoi et al., Transcriptional determinants of individualized inflammatory responses at anatomically separate sites, J. Allergy Clin. Immunol., 141(2):805-808 (2018).
Tyring et al., Long-term safety and efficacy of 50 mg of etanercept twice weekly in patients with psoriasis, Arch. Dermatol., 143(6):719-26 (2007).
Ye et al., Abnormal epidermal barrier recovery in uninvolved skin supports the notion of an epidermal pathogenesis of psoriasis, J. Invest. Dermatol., 134(11):2843-6 (2014).
Zaba et al., Amelioration of epidermal hyperplasia by TNF inhibition is associated with reduced Th17 responses, J. Exp. Med., 204(13):3183-94 (2007).
Zaba et al., Effective treatment of psoriasis with etanercept is linked to suppression of IL-17 signaling, not immediate response TNF genes, J. Allergy Clin. Immunol., 124(5):1022-10.e1-395 (2009).
Szel et al., Comprehensive Proteomic Analysis Reveals Intermediate Stage of Non-Lesional Psoriatic Skin and Points out the Importance of Proteins Outside this Trend, *Scientific Reports*, 9(1):11382: 1-15 (2019).
Foulkes et al., A Framework for Multi-Omic Prediction of Treatment Response to Biologic Therapy for Psoriasis, *J. Invest. Derm.*, 139(1):100-107 (2018).
Coda et al., Global transcriptional analysis of psoriatic skin and blood confirms known disease-associated pathways and highlights novel genomic "hot spots" for differentially expressed genes, Genomics, 100: 18-26 (2012).
Holland et al., Keratin gene expression during the resolution of psoriatic plaques: effect of dithranol, PUVA, etretinate and hydroxyurea regimens, British Journal of Dermatology, 120:9-19 (1989).
Staquet et al., Keratin Polypeptide Profile in Psoriatic Epidermis Normalized by Treatment with Etretinate (Aromatic Retinoid Ro 10-9359), Archives of Dermatological Research, 275:124-129 (1983).

* cited by examiner

Normal Skin
Psoriatic Skin
USP18

IL36G
DEFB4
si-NC
si-USP18
mRNA expression
0.0
0.1
0.2
0.3
0.4
0.5
0.6
0.8
con
TNFA
IL17A
TNFA+IL17A
IFNA
IFNG
****

METHODS FOR DETERMINING RESPONSIVENESS TO ANTI-TUMOR NECROSIS FACTOR THERAPY IN THE TREATMENT OF PSORIASIS

FIELD

The disclosure generally relates to methods for determining responsiveness to anti-tumor necrosis factor (TNF) therapy in the treatment of psoriasis. In some aspects, the disclosure provides one or more biomarkers associated with predicting efficacy in anti-TNF treatment of subjects with psoriasis.

BACKGROUND

Psoriasis is an immune-mediated condition that affects the skin and joints of >100 million individuals worldwide. Since psoriatic patients have activated tumor necrosis factor alpha (TNFα) in both lesional skin and blood (Arican et al., Mediators Inflamm. 2005; 2005(5):273-9; Johansen et al., J Immunol. 2006;176(3):1431-8.), at least five different agents inhibiting tumor necrosis factor (TNF) have been developed and approved (Leonardi et al., N Engl J Med. 2003;349(21):2014-22; Gordon et al., J Amer Acad Dermatol 2006;55(4):598-606; Chaudhari et al., Lancet. 2001;357(9271):1842-7; Kavanaugh et al., Arthritis Rheum. 2009;60(4):976-86; Blauvelt et al., J Eur Acad Dermatol Venereol. 2019 March; 33(3):546-552. doi: 10.1111/jdv.15258. Epub 2018 Oct. 14) to treat moderate-to-severe psoriasis and psoriatic arthritis, making it one of the most commonly used biologic classes to treat psoriasis.

Etanercept (i.e, ENBREL®) was amongst the first anti-TNF drugs approved to treat psoriasis. Etanercept is a fusion protein composed of TNF receptor-2 fused to an IgG1 Fc chain, which binds and neutralizes soluble TNFα (Gisondi et al., Autoimmun Rev. 2007;6(8):515-9.). Studies have illustrated etanercept's efficacy in reducing TNFα expression in both uninvolved and lesional skin, and in decreasing TFNα inducible receptor expression after treatment (Caldarola et al, Int J Immunopathol Pharmacol. 2009; 22(4):961-6.). TNF inhibition also has been shown to associate with reduced Th17 responses, thus improving epidermal hyperplasia for lesional skin (Zaba et al. J Exp Med. 2007; 204(13):3183-94). Prior studies have demonstrated that Th17 immune response is inactivated among responders to etanercept (Zaba et al., J Allergy Clin Immunol. 2009;124(5):1022-10 e1-395.). A double-blind study with 672 patients illustrated that etanercept increases the proportion of patients achieving PASI 75 (i.e., 75% improvement of psoriasis severity index) within 12 weeks of treatment (Leonardi, supra); however, similar to other anti-TNFα agents, patient outcomes for etanercept treatment vary, with PASI75 responses ranging from 23% to 60% depending on the study (Leonardi, supra, Krueger et al., J Amer Acad Dermatol 2006;54(3 Suppl 2):S112-9; Tyring et al., Arch Dermatol. 2007;143(6):719-26; Paller et al., J Amer Acad Dermatol 2010;63(5):762-8; Kivelevitch et al., Biologics. 2014; 8:169-82). Furthermore, the mechanisms involved remain unclear and are incompletely explained by psoriasis susceptibility genes (Foulkes et al., Br J Dermatol. 2017; 177(2): 344-5; Tsoi et al., J Allergy Clin Immunol. J Allergy Clin Immunol. 2018; 141(2): 805-808, Epub 2017 Oct. 13). Providing assessment of drug responses prior to treatment may enhance efficiency for treating mild-to-severe forms of psoriasis, limit the risk of unnecessary drug-exposures and reduce the economic burden for patients.

Precision medicine aims to provide personalized healthcare to patients based on their characteristics, and is an emerging research topic for different human diseases (Aziz et al., Crit Rev Oncol Hematol. 2017; 118: 70-8; Chan et al., Int J Mol Sci. 2017 Nov. 15; 18(11) 2423; Flamant et al., Therap Adv Gastroenterol. 2018; 11: 1-15; Horton et al, J Pers Med. 2017; 7(3): 7; Tavakolpour, Immunol Lett. 2017; 190: 130-8). Advancements in genomic research have facilitated precision medicine by using high throughput techniques to effectively reveal biomarkers and assess therapeutic options. However, its applications for complex skin conditions, including psoriasis, are still very limited, despite extensive transcriptomic studies have been conducted (Tsoi et al, supra; Li et al., J Invest Dermatol. 2014; 134(7):1828-38; Tsoi et al, Genome Biol. 2015; 16: 24; Gudjonsson et al., J Invest Dermatol. 2009; 129(12):2795-804; Gudjonsson et al., J Invest Dermatol. 2010;130(7):1829-40).

The art to date does not disclose methods for predicting efficacy of anti-TNF therapy in the treatment of psoriasis. Accordingly, a strong need in the art exists for a reliable way of predicting whether an anti-TNF agent would significantly aid in the prognosis and management of patients with psoriasis. The following disclosure describes the specifics of such biomarkers and their uses.

SUMMARY

The methods described herein were developed to provide a means for predicting outcome in the treatment of psoriasis with an anti-TNF agent. By applying statistical modeling using RNA-seq along with in vitro genomic data on cytokine responses for a cohort of etanercept treated psoriatic patients, the disclosure provides effective risk assessment for drug response. By demonstrating that transcriptome data correlates with treatment outcome, the disclosure demonstrates that gene expression changes in healthy appearing uninvolved skin is most predictive of therapeutic responses. Prior to this disclosure, studies focused on inflamed skin for identifying biomarkers. By using integrative approaches, methods for assessing future drug response have been developed.

In some aspects, the disclosure provides a method for treating psoriasis in a subject, the method comprising measuring a level of at least one biomarker in a biological sample of uninvolved skin isolated from the subject, wherein the level of the biomarker is increased or decreased relative to a mean baseline level of the biomarker in uninvolved skin in a population of psoriatic patients indicating that the subject will be responsive to treatment with an anti-TNF agent; and administering to the subject indicated to be responsive to treatment an effective amount of an anti-TNF agent.

The disclosure provides a method for treating psoriasis in a subject, the method comprising measuring a level of at least one biomarker in a biological sample of uninvolved skin isolated from the subject prior to treatment with an anti-tumor necrosis factor (anti-TNF) agent, wherein the at least one biomarker is (a) ubiquitin specific protease 18 (USP18) and the level of USP18 is increased relative to a control level;

(b) keratin, type II cytoskeletal 2 epidermal (KRT2) and the level of KRT2 is decreased relative to a control level;

(c) interleukin 4 receptor (IL4R) and the level of IL4R is increased relative to a control level;

(d) sex-determining region Y-box transcription factor 5 (SOX5), and the level of SOX5 is decreased relative to a control level;
(e) interferon induced with helicase C domain 1 (IFIH1), and the level of IFIH1 is increased relative to a control level; or
(f) a combination of biomarkers of any two or more of (a)-(e),
wherein the increased or decreased level of the biomarker in the subject relative to the control level predicts that the subject will be responsive to treatment with the anti-TNF agent, and
wherein the control level is the mean level of the biomarker in uninvolved skin in a population of subjects suffering from psoriasis prior to treatment with the anti-TNF agent; and
administering an effective amount of an anti-TNF agent to the subject predicted to be responsive to treatment.

In some aspects, the at least one biomarker is USP18. In some aspects, the at least one biomarker is KRT2. In some aspects, the at least one biomarker is IL4R. In some aspects, the at least one biomarker is SOX5. In some aspects, the at least one biomarker is IFIH1. In some aspects, the at least one biomarker is a combination of any two or more of USP18, KRT2, IL4R, SOX5, and IFIH1. In some aspects, the at least one biomarker is a combination of any two or more of USP18, KRT2, IL4R, SOX5, or IFIH1 as set out in any of the combinations in Table 1.

In some aspects, the level of USP18 is increased by at least about 86% or more relative to the control level. In some aspects, the level of KRT2 is decreased by at least about 99% or more relative to the control level. In some aspects, the level of IL4R is increased by at least about 36% or more relative to the control level. In some aspects, the level of SOX5 is decreased by at least about 89% or more relative to the control level. In some aspects, the level of IFIH1 is increased by at least about 49% or more relative to the control level.

In some aspects, the level is a measure of the level of a nucleic acid or protein present in the biological sample. In some aspects, the nucleic acid is deoxyribonucleic acid. In some aspects, the nucleic acid is ribonucleic acid.

In some aspects, the anti-TNF agent is etanercept, infliximab, adalimumab, certolizumab pegot, or golimumab or a biosimilar thereof. In some aspects, the anti-TNF agent is thalidomide, lenalidomide, pomalidomide, a xanthine derivative, or bupropion.

In some aspects, the psoriasis is plaque psoriasis, guttate psoriasis, inverse psoriasis, intertriginous psoriasis, pustular psoriasis, erythrodermic psoriasis, or psoriatic arthritis.

In some aspects, the method further comprises administering to the subject at least one additional treatment or medication for psoriasis.

In some aspects, the subject is a human subject.

In some aspects, the level of the biomarker is measured with an immunoassay, Northern blot analysis, reverse transcription quantitative polymerase chain reaction, RNA sequencing, or high-throughput sequencing.

In some aspects, the subject treated with the anti-TNF agent shows PASI improvement by about 12 weeks of treatment. In some aspects, PASI improvement is observed earlier than 12 weeks after treatment. In some aspects, the PASI improvement is at least about 10% of PASI improvement.

The disclosure provides a method for prognosing responsiveness to an anti-TNF agent in treatment of psoriasis in a subject, the method comprising measuring a level of at least one biomarker in a biological sample of uninvolved skin isolated from the subject prior to treatment with an anti-tumor necrosis factor (anti-TNF) agent, wherein the at least one biomarker is
(a) ubiquitin specific protease 18 (USP18);
(b) keratin, type II cytoskeletal 2 epidermal (KRT2);
(c) interleukin 4 receptor (IL4R);
(d) sex-determining region Y-box transcription factor 5 (SOX5);
(e) interferon induced with helicase C domain 1 (IFIH1); or
(f) a combination of biomarkers of any two or more of (a)-(e), and
comparing the level with a control level, wherein the control level is the mean level of the biomarker in uninvolved skin in a population of subjects suffering from psoriasis prior to treatment with the anti-TNF agent,
wherein when the level of USP18, ILR4, and/or IFIH1 in the subject is increased relative to the control level of the biomarker, the subject is predicted to be responsive to treatment with the anti-TNF agent;
wherein when the level of KRT2 and/or SOX5 in the subject is decreased relative to the control level of the biomarker, the subject is predicted to be responsive to treatment with the anti-TNF agent;
wherein when the level of USP18, ILR4, and/or IFIH1 in the subject is not increased relative to the control level of the biomarker, the subject is predicted to be non-responsive to treatment with the anti-TNF agent; and/or
wherein when the level of KRT2 and/or SOX5 in the subject is not decreased relative to the control level of the biomarker, the subject is predicted to be non-responsive to treatment with the anti-TNF agent.

In some aspects, the method for prognosing responsiveness further comprises administering an effective amount of the anti-TNF agent to treat the subject predicted to be responsive to treatment with the anti-TNF agent.

In some aspects, the at least one biomarker is USP18. In some aspects, the at least one biomarker is KRT2. In some aspects, the at least one biomarker is IL4R. In some aspects, the at least one biomarker is SOX5. In some aspects, the at least one biomarker is IFIH1. In some aspects, the at least one biomarker is a combination of any two or more of USP18, KRT2, IL4R, SOX5, or IFIH1. In some aspects, the at least one biomarker is a combination of any two or more of USP18, KRT2, IL4R, SOX5, or IFIH1 as set out in any of the combinations in Table 1.

In some aspects, the level of USP18 is increased by at least about 86% or more relative to the control level. In some aspects, the level of KRT2 is decreased by at least about 99% or more relative to the control level. In some aspects, the level of IL4R is increased by at least about 36% or more relative to the control level. In some aspects, the level of SOX5 is decreased by at least about 89% or more relative to the control level. In some aspects, the level of IFIH1 is increased by at least about 49% or more relative to the control level.

In some aspects, the level is a measure of the level of a nucleic acid or protein present in the biological sample. In some aspects, the nucleic acid is deoxyribonucleic acid. In some aspects, the nucleic acid is ribonucleic acid.

In some aspects, the anti-TNF agent is etanercept, infliximab, adalimumab, certolizumab pegot, or golimumab or a biosimilar thereof. In some aspects, the anti-TNF agent is thalidomide, lenalidomide, pomalidomide, a xanthine derivative, or bupropion.

In some aspects, the psoriasis is plaque psoriasis, guttate psoriasis, inverse psoriasis, intertriginous psoriasis, pustular psoriasis, erythrodermic psoriasis, or psoriatic arthritis.

In some aspects, the method further comprises administering to the subject at least one additional treatment or medication for psoriasis.

In some aspects, the subject is a human subject.

In some aspects, the level of the biomarker is measured with an immunoassay, Northern blot analysis, reverse transcription quantitative polymerase chain reaction, RNA sequencing, or high-throughput sequencing.

In some aspects, the subject treated with the anti-TNF agent shows PASI improvement by about 12 weeks of treatment. In some aspects, PASI improvement is observed earlier than 12 weeks after treatment. In some aspects, the PASI improvement is at least about 10% of PASI improvement.

The disclosure provides a kit comprising reagents for measuring a level of at least one biomarker in a biological sample of uninvolved skin isolated from a subject suffering from psoriasis prior to treatment with an anti-tumor necrosis factor (anti-TNF) agent, wherein the at least one biomarker is (a) ubiquitin specific protease 18 (USP18);

(b) keratin, type II cytoskeletal 2 epidermal (KRT2);

(c) interleukin 4 receptor (IL4R);

(d) sex-determining region Y-box transcription factor 5 (SOX5);

(e) interferon induced with helicase C domain 1 (IFIH1); or (f) a combination of biomarkers of any two or more of (a)-(e), and wherein the level is the level of nucleic acid or protein of the biomarker in the biological sample.

In some aspects, the kit further comprises a means for comparing the level of the nucleic acid or protein of the biomarker in the biological sample with a control level, wherein the control level is the mean level of the biomarker in uninvolved skin in a population of subjects suffering from psoriasis prior to treatment with the anti-TNF agent. In some aspects, the biological sample is obtained from a biopsy of uninvolved skin from a subject suffering from psoriasis. In some aspects, the biological sample is obtained from a biopsy of uninvolved skin from a subject suffering from psoriasis prior to treatment with an anti-TNF agent.

The disclosure provides use of measurement of an increased or decreased level of at least one biomarker in a biological sample of uninvolved skin from a subject suffering from psoriasis in comparison to measurement of a control level, wherein the control level is the mean level of the biomarker in uninvolved skin in a population of subjects suffering from psoriasis prior to treatment with the anti-TNF agent, for prognosing responsiveness of the subject to treatment with an anti-tumor necrosis factor (anti-TNF) agent, wherein the at least one biomarker is (a) ubiquitin specific protease 18 (USP18);

(b) keratin, type II cytoskeletal 2 epidermal (KRT2);

(c) interleukin 4 receptor (IL4R);

(d) sex-determining region Y-box transcription factor 5 (SOX5);

(e) interferon induced with helicase C domain 1 (IFIH1); or (f) a combination of biomarkers of any two or more of (a)-(e), and wherein when the level of USP18, ILR4, and/or IFIH1 in the subject is increased relative to the control level of the biomarker, the subject is predicted to be responsive to treatment with the anti-TNF agent;

wherein when the level of KRT2 and/or SOX5 in the subject is decreased relative to the control level of the biomarker, the subject is predicted to be responsive to treatment with the anti-TNF agent;

wherein when the level of USP18, ILR4, and/or IFIH1 in the subject is not increased relative to the control level of the biomarker, the subject is predicted to be non-responsive to treatment with the anti-TNF agent; and/or wherein when the level of KRT2 and/or SOX5 in the subject is not decreased relative to the control level of the biomarker, the subject is predicted to be non-responsive to treatment with the anti-TNF agent.

In some aspects, the at least one biomarker is USP18. In some aspects, the at least one biomarker is KRT2. In some aspects, the at least one biomarker is IL4R. In some aspects, the at least one biomarker is SOX5. In some aspects, the at least one biomarker is IFIH1. In some aspects, the at least one biomarker is a combination of any two or more of USP18, KRT2, IL4R, SOX5, or IFIH1. In some aspects, the at least one biomarker is a combination of any two or more of USP18, KRT2, IL4R, SOX5, or IFIH1 as set out in any of the combinations in Table 1.

In some aspects, the level of USP18 is increased by at least about 86% or more relative to the control level. In some aspects, the level of KRT2 is decreased by at least about 99% or more relative to the control level. In some aspects, the level of IL4R is increased by at least about 36% or more relative to the control level. In some aspects, the level of SOX5 is decreased by at least about 89% or more relative to the control level. In some aspects, the level of IFIH1 is increased by at least about 49% or more relative to the control level.

In some aspects, the level is a measure of the level of a nucleic acid or protein present in the biological sample. In some aspects, the nucleic acid is deoxyribonucleic acid. In some aspects, the nucleic acid is ribonucleic acid.

In some aspects, the anti-TNF agent is etanercept, infliximab, adalimumab, certolizumab pegot, or golimumab or a biosimilar thereof. In some aspects, the anti-TNF agent is thalidomide, lenalidomide, pomalidomide, a xanthine derivative, or bupropion.

In some aspects, the psoriasis is plaque psoriasis, guttate psoriasis, inverse psoriasis, intertriginous psoriasis, pustular psoriasis, erythrodermic psoriasis, or psoriatic arthritis.

In some aspects, the method further comprises administering to the subject at least one additional treatment or medication for psoriasis.

In some aspects, the subject is a human subject.

In some aspects, the level of the biomarker is measured with an immunoassay, Northern blot analysis, reverse transcription quantitative polymerase chain reaction, RNA sequencing, or high-throughput sequencing.

In some aspects, the subject treated with the anti-TNF agent shows PASI improvement by about 12 weeks of treatment. In some aspects, PASI improvement is observed earlier than 12 weeks after treatment. In some aspects, the PASI improvement is at least about 10% of PASI improvement.

In various aspects, the disclosure includes methods, kits, and uses of any one biomarker or combination of biomarkers disclosed herein for the prognosis and treatment of psoriasis based upon the expression of the biomarker or a combination of biomarkers.

This disclosure also provides a method for determining if a biomarker will be predictive of whether a subject suffering from psoriasis will respond to treatment with an anti-TNF agent, the method comprising (1) measuring the level of expression of one or more TNF-induced and/or or interferon (IFN)-induced genes in a biopsy of uninvolved skin and PASI score in a population of subjects suffering from psoriasis prior to treatment with the anti-TNF agent; (2) treating the population of subjects with an anti-TNF agent for at least about 12 weeks; (3) track changes of the transcriptomes over the treatment course; and (4) identify differentially expressed transcripts associated with improved PASI score after controlling for body mass index (BMI), gender, and age of the patients.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1A) shows the design of the study. FIG. 1B shows the top two principal components computed using transcriptomic data for all the RNA-seq samples. FIG. 1C shows a heatmap illustrating the change in expression profiles across the treatment time course. 46 patients were recruited in the cohort, with 42 of the 46 patients providing RNA-seq data at both baseline and at least one of their follow-up visits.

FIG. 3A shows immunostaining for USP18 in uninvolved and lesional psoriatic skin, confirming its expression in the epidermal layer. siRNA was used to knockdown the expression of USP18 in keratinocytes and evaluate the impact on TNF/IFN responses (FIG. 3B-D). FIG. 3B shows the effect of depleting USP18 on type I and type II stimulations (x-axis). FIG. 3B shows the effect of depleting USP18 on the expression of IL36G and DEFB4 after stimulation with TNF, IL-17A, IFN-α or IFN-γ (x-axis). FIG. 3C shows the effect of depleting USP18 on the expression of myxovirus (influenza virus) resistance 1 (interferon-inducible Protein P78; MX1) and interferon-kappa (IFNK) after stimulation with IFN-α or IFN-γ (x-axis). FIG. 3D shows the effect of depleting USP18 on the expression of oligoadenylate synthetase-like protein (OASL) and interferon regulatory factor 7 (IRF7) after stimulation with IFN-α or IFN-γ (x-axis). FIG. 3E-G shows the effect of USP18 overexpression on type I and type I IFN responses. FIG. 3E shows the effect of USP18 overexpression on the expression of interleukin-36 gamma (IL36G) and defensing beta 4 (DEFB4) after stimulation with TNF, IL-17A, IFN-α and IFN-y. FIG. 3F shows the effect of USP18 overexpression on the expression of MX1 and IFNK after stimulation with IFN-α and IFN-y. FIG. 3G shows the effect of USP18 overexpression on the expression of OASL after stimulation with IFN-α and IFN-γ. FIG. 3H shows a Western blot confirming increased USP18 protein levels in USP18 plasmid transfected cells. Data shown with STDV and are representative of 3 biologic replicates. *$p<0.05$, $p<0.01$, *$p<0.001$.

FIG. 4A shows enrichment of the signatures among genes showing strongest differential expression in lesional skin between baseline versus follow-up. FIG. 4B-C shows enrichment of the signatures among expression profiles at baseline in uninvolved skin (b) or lesional skin (c) showing strongest association with follow-up PASI improvement.

FIG. 5A-B shows each patient's TNF score at baseline: uninvolved skin (x-axis) was plotted against the patient's IFN score, and the color scheme represents the PASI improvement by week 12 using either absolute (FIG. 5A) or percent (FIG. 5B) measure. FIG. 5C shows the AUROC values when using different number of principal components (PCs) in the model. PCs were computed using IFN/TNF induced genes. FIG. 5D shows how precision (solid line) and recall (dotted line) were plotted against the top proportion of samples predicted to achieve PASI 75 by week 12.

DETAILED DESCRIPTION

Figure 1A:
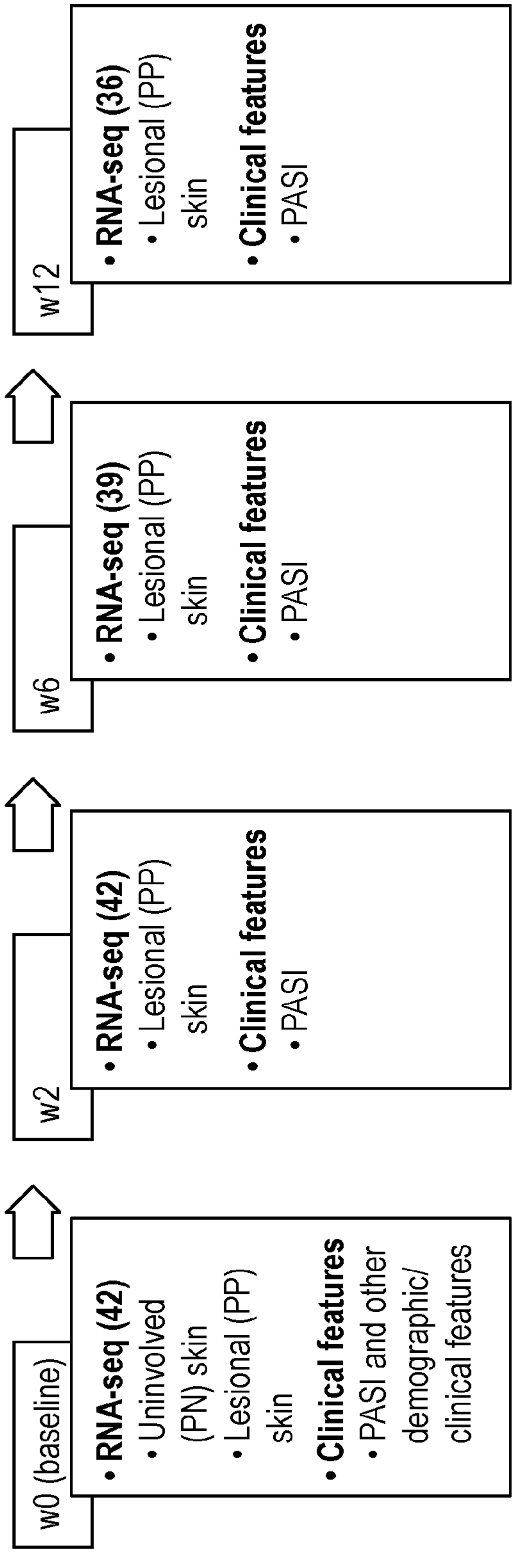
FIG. 1A-C depicts a transcriptome of the longitudinal cohort.

The disclosure relates to the identification of various biomarkers, alone and in combination, as predictors of treatment outcome of psoriasis with an anti-TNF agent.

More specifically, the disclosure provides fast and robust methods of predicting efficacy of treatment with an anti-TNF agent by measuring a level of at least one biomarker in a biological sample of uninvolved skin isolated from a subject suffering from psoriasis, wherein a change in the level of the biomarker in uninvolved skin of the subject compared to a baseline level of the biomarker indicates whether the subject will be responsive to treatment with the anti-TNF agent. In some aspects, the methods of the disclosure include administering to the subject predicted to be responsive to treatment an effective amount of an anti-TNF agent.

Before any embodiments of the subject matter of the disclosure are explained in detail, it is to be understood that the disclosure is not limited in its application to the details of construction and the arrangement of components set forth in the following description or illustrated in the figures and examples. Accordingly, the disclosure embraces other embodiments and is practiced or carried out in various ways.

The section headings as used herein are for organizational purposes only and are not to be construed as limiting the subject matter described.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

A "control" refers to an active, positive, negative or vehicle control. In the disclosure, the "control" or "control level" provides a comparison for measuring the level or amount of biomarker present in uninvolved skin in a subject. Thus, the "control" or "control level," as used herein, is a mean level of the biomarker in uninvolved skin in a population of psoriatic patients at baseline, i.e., at day 0 or prior to any treatment with an anti-TNF agent. In some aspects, the relative level of expression of the nucleic acid in a sample from a subject is compared to the control level. Thus, some measurements are expressed as relative to the control. In some aspects, the control level is the mean of the normalized read count of a gene across samples, i.e., mean control level of the biomarker at baseline. In some aspects, the population of psoriatic patients is at least about 20, at least about 25, at least about 30, at least about 35, at least about 40, at least about 45, or at least about 50 psoriatic patients. In some aspects, the population of psoriatic patients is at least about 35 psoriatic patients. In some aspects, the population of psoriatic patients is at least about 36 psoriatic patients. In some aspects, the population of psoriatic patients in the control may be increased.

"Measuring" or "measurement" means assessing the presence, quantity or level of a substance, e.g. a biomarker, within a clinical or subject-derived sample, including the derivation of qualitative or quantitative concentration levels of such substance, or otherwise evaluating the values or categorization of a subject's clinical parameters. Recitation of ranges of values herein are merely intended to serve as a shorthand method for referring individually to each separate value falling within the range and each endpoint, unless otherwise indicated herein, and each separate value and endpoint is incorporated into the specification as if it were individually recited herein.

The terms "level" and "amount" are used herein interchangeably to mean the concentration of biomarker present in a biological sample. In some aspects of the disclosure, the biological sample is a biopsy or scraping of uninvolved skin in a psoriatic patient (i.e., subject) or a population of psoriatic patients (i.e., subjects). In some aspects, nucleic acid and/or protein is prepared from the sample of uninvolved skin and the "level" and/or "amount" is the level or amount of a particular nucleic acid and/or protein of interest. In some aspects, it is the level or amount of the nucleic acid and/or protein biomarker.

The terms "protein," "polypeptide," and "peptide" are used interchangeably herein to refer to a polymer of amino acid residues linked via peptide bonds. The term "protein" typically refers to large polypeptides. The term "peptide" typically refers to short polypeptides.

The term "nucleic acid" or "nucleic acid sequence" or "nucleic acid molecule" refers to deoxyribonucleotides or ribonucleotides and polymers thereof in either single- or double-stranded form. The term nucleic acid is used interchangeably with gene, deoxyribonucleic acid, complementary DNA (cDNA), ribonucleic acid, messenger RNA (mRNA), oligonucleotide, and polynucleotide.

As used herein, a "fragment" of a protein or a nucleic acid refers to any portion of the protein or nucleic acid smaller than the full-length protein, nucleic acid, or protein expression product. Fragments are deletion analogs of the full-length protein or nucleic acid wherein one or more amino acid residues (protein) or nucleotides (nucleic acid) have been removed from the amino terminus (protein) or 5' end (nucleic acid) and/or the carboxy terminus (protein) or 3' end (nucleic acid) of the full-length protein or nucleic acid.

Biomarkers

In various aspects, the disclosure includes methods of measuring a biomarker in a biological sample from a subject, wherein the presence of the biomarker at an increased level over control or at a decreased level under control indicates the subject will favorably respond to treatment with an anti-TNF agent.

A "biomarker" in the context of the disclosure encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. In some aspects, therefore, a biomarker includes a protein or a fragment thereof or a nucleic acid or a fragment thereof. In some aspects, the biomarker is a TNF-induced or IFN-induced nucleic acid or protein. In additional aspects, one or more biomarkers are measured together to provide an array for the prediction that the subject will positively respond to an anti-TNF therapy in the treatment of psoriasis. A biomarker of the discosure is any one or more of ubiquitin specific protease 18 (USP18), keratin, type II cytoskeletal 2 epidermal (KRT2), Interleukin 4 Receptor (IL4R), SRY-Box 5 (SOX5), or Interferon Induced With Helicase C Domain 1 (IFIH1). In exemplary aspects, the term "USP18," as used herein, refers to a USP18 protein or nucleic acid; the term "KRT2," as used herein, refers to a KRT2 protein or nucleic acid; the term "IL4R," as used herein, refers to an IL4R protein or nucleic acid; the term "SOX5," as used herein, refers to a SOX5 protein or nucleic acid; and the term "IFIH1," as used herein, refers to an IFIH1protein or nucleic acid.

In some aspects, the methods include measuring the level of one or more of USP18, KRT2, IL4R, SOX5, and/or IFIH1 protein or nucleic acid in a biological sample. In some aspects, the methods further comprise measuring the level of an additional biomarker or a combination of biomarkers shown to correlate with an improvement in psoriasis in a subject suffering therefrom. The disclosure includes the use of one or more of these biomarkers in methods of predicting success of anti-TNF treatment in a patient suffering from psoriasis.

The disclosure includes the use of any one biomarker or combination of biomarkers listed in the table of biomarkers below in any of the disclosed methods, kits, uses and the like. For example, the disclosure, in various aspects, includes any biomarker or combination of biomarkers as illustrated in columns 1-26 in Table 1 below.

TABLE 1

Biomarkers and Combinations of Biomarkers.

| Column No. | USP18 | KRT2 | IL4R | SOX5 | IFIH1 |
|---|---|---|---|---|---|
| 1 | X | | | | |
| 2 | X | X | | | |
| 3 | X | | X | | |
| 4 | X | | | X | |
| 5 | X | | | | X |
| 6 | | X | | | |
| 7 | | X | X | | |
| 8 | | X | | X | |
| 9 | | X | | | X |
| 10 | | | X | | |
| 11 | | | X | X | |
| 12 | | | X | | X |
| 13 | | | | X | |
| 14 | | | | X | X |
| 15 | | | | | X |
| 16 | X | X | X | | |
| 17 | X | X | | X | |
| 18 | X | X | | | X |
| 19 | | X | X | X | |
| 20 | | | X | X | X |
| 21 | | X | X | | X |
| 22 | X | X | X | X | |
| 23 | X | X | | X | X |
| 24 | X | | X | X | X |
| 25 | | X | X | X | X |
| 26 | X | X | X | X | X |

Prognostic Value of Biomarker Level in the Treatment of Psoriasis

In the disclosure, a significant increase or decrease in the level of each of five biomarkers is each independently correlated with a positive response to treatment with an anti-TNF agent in a patient suffering from psoriasis. For each biomarker (gene), the expression level in uninvolved skin at baseline was correlated with the PASI change at week 12, adjusting for the body mass index (BMI), gender, and age of the patient (e.g., by treating these variables as covariates in the regression framework). Each of these five biomarkers was selected because it encodes a protein which has been shown to be involved in the immune process and because it was among the top 20 most significant genes associated with a positive response to treatment with an anti-TNF agent in a patient suffering from psoriasis.

In the disclosure, the level of a biomarker is measured in a sample from a subject suffering from psoriasis and compared to the control, which is the mean level of the biomarker from uninvolved skin from a population of psoriatic patients. In various aspects, an increased level of biomarker is a level significantly greater than the control level. In various aspects, an increase in the level of the biomarker in a subject is at least or about 1% greater, at least or about 2% greater, at least or about 3% greater, at least or about 4% greater, at least or about 5% greater, at least or about 6% greater, at least or about 7% greater, at least or about 8% greater, at least or about 9% greater, at least or about 10% greater, at least or about 11% greater, at least or about 12% greater, at least or about 13% greater, at least or about 14% greater, at least or about 15% greater, at least or about 16% greater, at least or about 17% greater, at least or about 18% greater, at least or about 19% greater, at least or about 20% greater, at least or about 21% greater, at least or about 22% greater, at least or about 23% greater, at least or about 24% greater, at least or about 25% greater, at least or about 26% greater, at least or about 27% greater, at least or about 28% greater, at least or about 29% greater, at least or about 30% greater, at least or about 35% greater, at least or about 40% greater, at least or about 45% greater, at least or about 50% greater, at least or about 55% greater, at least or about 60% greater, at least or about 65% greater, at least or about 70% greater, at least or about 75% greater, at least or about 80% greater, at least or about 85% greater, at least or about 90% greater, at least or about 95% greater, at least or about 100% greater, at least or about greater than 100% greater than the level of the control. In exemplary aspects, the control level is a mean level of the biomarker in a biological sample of uninvolved skin from a population of psoriatic patients prior to treatment with an anti-TNF agent (i.e., baseline).

In additional aspects, an increase in the level of the biomarker in a subject is at least or about 1/10 greater, at least or about 1/9 greater at least or about 1/8 greater, at least or about 1/7 greater, at least or about 1/6 greater, at least or about 1/5 greater, at least or about 1/4 greater, at least or about 1/3 greater, at least or about 1/2 greater, at least or about 1 times greater, at least or about 1.5 times greater, at least or about 2.0 times greater, at least or about 2.5 times greater, at least or about 3.0 times greater, at least or about 3.5 times greater, at least or about 4.0 times greater, at least or about 4.5 times greater, at least or about 5 times greater than the control level.

In other aspects, an increased level of a biomarker in a sample means that the concentration of the biomarker is significantly greater than the control level. Significant differences are calculated according to any statistical analysis method known to one of ordinary skill in the art.

In the disclosure, the level of a biomarker is measured in a sample from a subject suffering from psoriasis and compared to the level of the biomarker in a control. In various aspects, a decreased level of biomarker is a level significantly lesser than the control level. In various aspects, a decrease in the level of the biomarker in a subject is at least or about 1% lesser, at least or about 2% lesser, at least or about 3% lesser, at least or about 4% lesser, at least or about 5% lesser, at least or about 6% lesser, at least or about 7% lesser, at least or about 8% lesser, at least or about 9% lesser, at least or about 10% lesser, at least or about 11% lesser, at least or about 12% lesser, at least or about 13% lesser, at least or about 14% lesser, at least or about 15% lesser, at least or about 16% lesser, at least or about 17% lesser, at least or about 18% lesser, at least or about 19% lesser, at least or about 20% lesser, at least or about 21% lesser, at least or about 22% lesser, at least or about 23% lesser, at least or about 24% lesser, at least or about 25% lesser, at least or about 26% lesser, at least or about 27% lesser, at least or about 28% lesser, at least or about 29% lesser, at least or about 30% lesser, at least or about 35% lesser, at least or about 40% lesser, at least or about 45% lesser, at least or about 50% lesser, at least or about 55% lesser, at least or about 60% lesser, at least or about 65% lesser, at least or about 70% lesser, at least or about 75% lesser, at least or about 80% lesser, at least or about 85% lesser, at least or about 90% lesser, at least or about 95% lesser, at least or about 100% lesser, or about lesser than 100% lesser than the level of the control. In exemplary aspects, the control level is a mean level of the biomarker in a biological sample of uninvolved skin from a population of psoriatic patients prior to treatment with an anti-TNF agent (i.e., baseline).

In additional aspects, a decrease in the level of the biomarker in a subject is at least or about 1/10 lesser, at least or about 1/9 lesser at least or about 1/8 lesser, at least or about 1/7 lesser, at least or about 1/6 lesser, at least or about 1/5 lesser, at least or about 1/4 lesser, at least or about 1/3 lesser, at least or about 1/2 lesser, at least or about 1 times lesser, at least or about 1.5 times lesser, at least or about 2.0 times lesser, at least or about 2.5 times lesser, at least or about 3.0 times lesser, at least or about 3.5 times lesser, at least or about 4.0 times lesser, at least or about 4.5 times lesser, or at least or about 5 times lesser than the control level.

In other aspects, a decreased level of a biomarker in a sample means that the concentration of the biomarker is significantly lesser than the control level. Significant differences are calculated according to any statistical analysis method known to one of ordinary skill in the art.

In some aspects, the disclosure provides the relative level of biomarker expression at day 0 in uninvolved skin to be predictive of improvement in psoriasis when treated with an anti-TNF agent. It was determined for a subject to achieve an approximate average 10 point improvement in PASI score by week 12 of treatment with an anti-TNF agent that the expression level of the biomarker at week 0 in uninvolved skin would be as follows:

(1) for USP18: an expression level at day 0 in uninvolved skin of at least about 86% greater than the mean expression level of USP18 in uninvolved skin of psoriatic patients at week 0;
(2) for IL4R: an expression level at day 0 in uninvolved skin of at least about 36% greater than the mean expression level of IL4R in uninvolved skin of psoriatic patients at week 0;
(3) for IFIH1: an expression level at day 0 in uninvolved skin of at least about 49% greater than the mean expression level of IFIH1 in uninvolved skin of psoriatic patients at week 0;
(4) for SOX5: an expression level at day 0 in uninvolved skin of at least about 89% lesser than the mean expression level of SOX5 in uninvolved skin of psoriatic patients at week 0; and
(5) for KRT2: an expression level at day 0 in uninvolved skin of at least about 99% lesser than the mean expression level of KRT2 in uninvolved skin of psoriatic patients at week 0.

In other words, if a subject is determined to have a USP18 level at day 0 in uninvolved skin of at least about 86% greater than the control (i.e., the mean expression level of the biomarker in uninvolved skin in a population of psoriatic patients at baseline or week 0), or a IL4R level of at least about 36% greater than the control, or an IFIH1 level of at least about 49% greater than the control, or a SOX5 level of at least about 89% lesser than the control, or a KRT2 level of at least about 99% lesser than the control, the subject is predicted to have an average 10 point improvement in PASI score by week 12 of treatment with an anti-TNF agent.

In some aspects of the disclosure, the level of biomarker in a biological sample (e.g., a biopsy of uninvolved skin from a subject suffering from psoriasis prior to treatment with an anti-TNF agent) is compared to a control level. The control level is the mean level of biomarker from a skin biopsy from a population of psoriatic subjects, wherein the skin biopsy is taken at day 0 or prior to treatment with the anti-TNF agent (i.e., baseline). In some aspects, the population of subjects is, optionally, matched to the subject in other parameters, such as one or more of the following: age, sex, severity of psoriasis and the like. In various aspects, the level of the biomarker is a relative level. In some aspects, the level of the biomarker is an absolute level.

Detecting and Measuring Biomarker Level

In various aspects of the disclosure, level of the protein biomarker is detected or quantitatively measured in a biological sample by any suitable means known in the art for quantifying protein including, but not limited to, immunoassay (e.g., ELISA, RIA), immunoturbidimetry, rapid immunodiffusion, laser nephelometry, visual agglutination, quantitative Western blot analysis, multiple reaction monitoring-mass spectrometry (MRM Proteomics), Lowry assay, Bradford assay, BCA assay, and UV spectroscopic assays, such as a UV spectroscopic assay. Alternatively, Northern blotting can be used to compare the levels of mRNA.

In various aspects of the disclosure, level of the nucleic acid biomarker is detected or quantitatively measured in a biological sample by any suitable means known in the art for quantifying nucleic acid including, but not limited to, RNA sequencing (RNA-seq), high-throughput sequencing (HT-seq), PCR, quantitiative PCR, qT-PCR, RT-qPCR, digital PCR, real-time PCR, direct digital quantification, serial analysis of gene expression (SAGE), nucleic acid sequence—based amplification (NASBA), transcription-mediated amplification (TMA), branched DNA (bDNA) assays, and/or Northern or Southern blotting.

RNA sequencing or "RNA seq," as used herein, is used in various aspects of the disclosure. RNA seq, also called whole transcriptome shotgun sequencing (WTSS), uses next-generation sequencing (NGS) to reveal the presence and quantity of RNA in a biological sample at a given moment. RNA-Seq, in some aspects, is used to analyze the continuously changing cellular transcriptome, which is the total cellular content of RNAs including mRNA, rRNA and tRNA. Understanding the transcriptome is key to connect information on one's genome with its functional protein expression. RNA-seq is a tool to observe which genes are turned on in a cell, what their level of expression is, and at what times they are activated or shut off, allowing scientists to better understand the biology of a cell and assess changes that may indicate disease. This can give researchers vital information about the function of genes in cells and tissues. In some aspects, the RNA seq or HT-seq provides relative levels of the biomarker compared to the control. In some aspects, the level of the biomarker is quantified using standard methods used in RNA-seq data analysis, including transcript quantification (Conesa et al., Genome Biol 2016; 17:13). In some aspects, the relative level of nucleic acid, is measured by an method of measuring nucleic acid known in the art. The quantitation of nucleic acids is commonly performed to determine the average concentrations of nucleic acid, either DNA or RNA, present in a sample. In some aspects, the quantification is carried out by PCR, qPCR, spectrophotometric quantification, and/or by UV fluorescence tagging in presence of a nucleic acid dye.

In exemplary aspects, 50 bp single-ended reads are generated from RNA-seq samples from patients. For each sequence file, trimmomatic is used to conduct adapter trimming (Bolger et al., Bioinformatics 2014; 30(15):2114-20), and STAR (Dobin et al., Bioinformatics. 2013; 29(1):15-21) is used for aligning the reads to human genome b37. HTSeq is employed for expression level quantification (Anders et al., Bioinformatics 2015;31(2):166-9).

In various aspects, any of these methods is performed using a nucleic acid (e.g., DNA, cDNA, RNA, or mRNA) or protein of a biological sample obtained from a biopsy of skin from a human subject suffering from psoriasis. In exemplary aspects, the biological sample is from uninvolved skin. In additional exemplary aspects, the sample is taken prior to treatment with an anti-TNF agent to measure the level of the biomarker before treatment. In some aspects, the sample is taken during and after treatment with an anti-TNF agent to measure the level of the biomarker during or after treatment.

In some aspects, the Area under the Receiver Operating Characteristic (AUROC) is measured. AUROC is a common summary statistic for the goodness of a predictor in a binary classification task. It is equal to the probability that a predictor will rank a randomly chosen positive instance higher than a randomly chosen negative one. Specificity and sensitivity are best represented by an AUROC curve which is a plot of the false positive rate on the x axis and true positive rate on the y axis for every possible level of a marker. A perfect test would have an AUROC curve that is a right angle demonstrating 100% of true positives and no false positives. In this case, the corresponding AUROC equals 1. A random test has an AUROC of 0.5, meaning that there is one false positive for every true positive. A biomarker panel, in various aspects, includes several biomarkers that together are diagnostic or predictive.

Psoriasis

In various aspects, the methods of the disclosure are applicable to patients with psoriasis. Psoriasis is a genetic, immune-mediated disease, affecting 1-3% of the US population. About 30% of patients with psoriasis are also affected by psoriatic arthritis (PsA), which is associated with a wide variety of additional symptoms that contribute to the disease burden. Thus, the term "psoriasis," as used in the disclosure, includes, but is not limited to, plaque psoriasis, guttate psoriasis, inverse psoriasis, intertriginous psoriasis, pustular psoriasis, erythrodermic psoriasis, or PsA. Factors such as joint pain, erosive joint damage, enthesitis, and dactylitis, as well as psoriasis of the skin and nails further increase the longterm effect on patients' quality of life, physical function, and ability to work.

Psoriasis is a chronic inflammatory skin disease characterized by infiltration of activated leukocytes and increased proliferation of epidermal keratinocytes. The importance of immunological mechanisms has been suggested in the pathogenesis of psoriasis, and the detection of cytokines in horny tissue extracts, suction blister fluids, cytosolic extracts and sera of psoriatic patients has been reported. In addition to the release by immune cells of inflammatory cytokines that may propagate psoriasis, keratinocytes produce a number of cytokines, including TNF, either spontaneously or after stimulation, with proinflammatory and growth-promoting activities.

The wide variety of symptoms makes evaluation of overall disease activity and response to therapy difficult in both psoriasis and PsA. Thus, accurate assessment is essential for the clinician to determine the most appropriate treatment. These assessment difficulties are particularly true of skin disease because of limitations of the currently used outcome measures. A subject or patient suffering from psoriasis is a patient who suffers from the classic symptoms of psoriasis and/or has been diagnosed by a medical professional as suffering from psoriasis.

Uninvolved Skin and Lesional Skin in Psoriasis

In various aspects, uninvolved skin is used in the methods of the disclosure. Uninvolved skin of psoriasis patients is normal appearing skin, which is non-inflamed. In various aspects, the biopsies of uninvolved skin are carried out on any normal appearing, non-inflamed skin not near a psoriatic lesion. In some aspects, the biopsy of uninvolved skin is carried out on the buttocks away from any active psoriatic lesions because such skin biopsies on the buttocks are more cosmetically acceptable and it is easier to hide any scar.

There is local diffusion of psoriasis; therefore, a person of ordinary skill in the art knows not to take a sample of uninvolved skin near diseased skin. As used herein, a "biological sample" taken from a subject is, in various aspects, a sample of uninvolved skin obtained from the subject. In various aspects, this sample is a biopsy of skin punch obtained from involved skin. In some aspects, the biopsy is obtained under local anesthesia (lidocaine 1:10,000 epinephrine) from both uninvolved and lesional skin. In some aspects, the biopsy is taken at baseline and then at measured time points thereafter. In some aspects, the biopsy is take at time 0 or baseline and then again at 2, 6 and 12 weeks. In various aspects, the biological sample or "sample" contains nucleic acid and/or protein and/or fluid containing organic and/or inorganic metabolites and substances. In some aspects of the invention, the sample comprises protein and nucleic acid suitable for measuring protein or nucleic acid level or for measuring protein or nucleic acid expression level. In exemplary aspects, quantity of RNA is measured using RNA-sequencing (RNA-seq).

It has been established in multiple studies that uninvolved skin from psoriatic patients is different than skin from healthy controls. This includes an elevated rate of epidermal proliferation in an in vivo xenograft model (Krueger et al., J Clin Invest. 1981;68(6)1 548-57), lower levels of epidermal barrier protein filaggrin and loricrin (Kim et al., J Invest Dermatol. 2011; 131(6):1272-9), changes in innate immune response and lipid metabolism genes (Gudjonsson et al., J Invest Dermatol. 2009; 129(12):2795-804), and an abnormal epidermal barrier recovery (Ye et al., J Invest Dermatol. 2014; 134(11):2843-6.). The reason for these changes in psoriatic skin are unclear but it has been speculated to be due to a systemic inflammatory response from increased levels of circulating pro-inflammatory mediators (Dowlatshahi et al., Br J Dermatol. 2013;169(2):266-82), genetic predisposition (Tsoi et al., Nature Genetics 2012;44(12)1 341-8; Tsoi et al., Nat Commun. 2017; 8: 15382), or a combination of both. Regardless of the mechanism, these pro-inflammatory signatures in uninvolved skin in some aspects provide unique characteristics for each patient's global inflammatory response.

Methods for Measuring Psoriasis Severity

In various aspects of the disclosure, psoriasis severity is measured by a physician or a physician's assistant. There are multiple systems used in clinical practice for measuring psoriasis severity including, but not limited to, the Lattice System Physician's Global Assessment (LS-PGA), Psoriasis Area and Severity Index ((PASI), also known as PASI score), static Physician's Global Assessment (sPGA or PGA), body surface area (BSA), and/or PGAxBSA.

The PASI score is the most widely used tool for the measurement of skin involvement and is considered the "gold standard" for clinical trials (Armstrong et al., JAMA Dermatol 2013;149:577-82). PASI combines the assessment of the severity of lesions and the area affected into a single score in the range 0 (no disease) to 72 (maximal disease). The PASI is an index used to express the severity of psoriasis, combining the severity (erythema, induration and desquamation) and percentage of affected area. An area and severity score for each region is calculated by multiplying the area score by the severity score (maximum 6×12=72). The amount each region contributes to the final PASI is then weighted according to how much of the total body skin surface it represents. In general, a PASI score below 10 defines psoriasis as mild, between 10 and 20 as moderate, and above 20 as severe. A 75% reduction in the PASI score (PASI 75) is the current benchmark of primary endpoints for most clinical trials of psoriasis; however, many consider this endpoint to be too stringent as it places potentially useful therapies at risk of failing to demonstrate efficacy. In some aspects of the disclosure, PASI 75 is used as an endpoint in the assessment of psoriasis. In some other aspects of the disclosure, however, change in the absolute value of the PASI score, e.g., a change of PASI score of about 10 points is used as an endpoint in the assessment of an improvement or a worsening of psoriasis. For example, a reduction in PASI score by about 10 reflects a 10 point improvement in the patient's PASI score and an improvement in the patient's psoriasis condition. To achieve or predict an average change in PASI score by about 10 points or greater by week 12 of treatment, the expression of biomarkers at day 0 in uninvolved skin are as follows:

(1) for USP18: an expression level at day 0 in uninvolved skin of at least about 86% greater than the mean expression level of USP18 in uninvolved skin of psoriatic patients at week 0;

(2) for IL4R: an expression level at day 0 in uninvolved skin of at least about 36% greater than the mean expression level of IL4R in uninvolved skin of psoriatic patients at week 0;

(3) for IFIH1: an expression level at day 0 in uninvolved skin of at least about 49% greater than the mean expression level of IFIH1 in uninvolved skin of psoriatic patients at week 0;

(4) for SOX5: an expression level at day 0 in uninvolved skin of at least about 89% lesser than the mean expression level of SOX5 in uninvolved skin of psoriatic patients at week 0; and (5) for KRT2: an expression level at day 0 in uninvolved skin of at least about 99% lesser than the mean expression level of KRT2 in uninvolved skin of psoriatic patients at week 0.

In other words, if a subject is determined to have a USP18 level at day 0 in uninvolved skin of at least about 86% greater than the control (i.e., the mean expression level of the biomarker in uninvolved skin in a population of psoriatic patients at week 0), or a IL4R level of at least about 36% greater than the control, or an IFIH1 level of at least about 49% greater than the control, or a SOX5 level of at least about 89% lesser than the control, or a KRT2 level of at least about 99% lesser than the control, the subject is predicted to have an average 10 point improvement in PASI score by week 12 of treatment with an anti-TNF agent.

In some aspects, it is predicted that the subject having a USP18 level at least about 20%, about 30%, about 40%, about 50%, about 60%, about 70%, or about 80% greater than the control level will have some improvement in PASI score by week 12 of treatment with an anti-TNF agent. In some aspects, it is predicted that the subject having an IL4R level at least about 10%, about 20%, or about 30% greater than the control level will have some improvement in PASI score by week 12 of treatment with an anti-TNF agent. In some aspects, it is predicted that the subject having an IFIH1 level at least about 10%, about 20%, about 30%, or about 40% greater than the control level will have some improvement in PASI score by week 12 of treatment with an anti-TNF agent. In some aspects, it is predicted that the subject having a SOX5 level at least about 20%, about 30%, about 40%, about 50%, about 60%, about 70%, or about 80% lesser than the control level will have some improvement in PASI score by week 12 of treatment with an anti-TNF agent. In some aspects, it is predicted that the subject having a KRT2 level at least about 20%, about 30%, about 40%, about 50%, about 60%, about 70%, about 80%, or about 90% lesser than the control level will have some improvement in PASI score by week 12 of treatment with an anti-TNF agent.

In some aspects, patients have a full clinical assessment at baseline (i.e., time 0), 2, 6 and 12 weeks by a dermatologist and BSA, PGA, and PASI scores are recorded.

Methods of Treatment of Psoriasis

In various aspects, the disclosure includes methods of treating psoriasis.

In some aspects, the disclosure provides various anti-TNF agents in the treatment of psoriasis. In various aspects any anti-TNF agent is used in the methods or uses of the disclosure. In some aspects, the anti-TNF agent is an anti-TNF-alpha (anti-TNFα) agent. In some aspects, the anti-TNF agent is etanercept, infliximab, adalimumab, certolizumab pegol, or golimumab, or a biosimilar thereof.

In some aspects, the anti-TNF agent is etanercept. Etanercept (e.g., ENBREL®) is available commercially and is an anti-TNF agent used to treat moderate-to-severe psoriasis, among other things. Etanercept treats autoimmune diseases by interfering with TNF, a soluble inflammatory cytokine, by acting as a TNF inhibitor. In some aspects, the anti-TNF agent is infliximab (e.g., REMICADE®). In some aspects, the anti-TNF agent is adalimumab (e.g., HUMIRA®). In some aspects, the anti-TNF agent is certolizumab pegol (e.g., CIMZIA®). In some aspects, the anti-TNF agent is golimumab (e.g., SIMPONI®).

In some aspects, the anti-TNF agent is a biosimilar to etanercept. In some aspects, the etanercept biosimilar is etanercept-ykro (Eticovo™) or etanercept-szzs (Erelzi™). In some aspects, the anti-TNF agent is a biosimilar to infliximab. In some aspects, the infliximab biosimilar is Remsima™ or infliximab-dyyb (Inflectra™). In some aspects, the anti-TNF agent is a biosimilar to adalimumab. In some aspects, the adalimumab biosimilar is adalimumab-atto (Amjevita™), adalimumab-bwwd (Hadlima™) or adalimumab-adaz (Hyrimoz™). In some aspects, the anti-TNF agent is a biosimilar to certolizumab pegol. In some aspects, the certolizumab pegol biosimilar is Xbrane™. In some aspects, the anti-TNF agent is a biosimilar to golimumab.

In other aspects, the anti-TNF agent is thalidomide, lenalidomide, pomalidomide, a xanthine derivative, or bupropion. In some aspects, it is possible that two or more anti-TNF agent is combined in a combination therapy. In some aspects, the anti-TNF agent is delivered with another drug or agent used in the treatment of psoriasis.

In some aspects, the disclosure includes additional treatments used in the treatment of psoriasis. In some aspects, such treatments are used in combination with treatment with an anti-TNF agent. These treatments can be used simultaneously or sequentially, either before or after treatment with an anti-TNF agent. Psoriasis treatments reduce inflammation and clear the skin. In some embodiments, treatments are divided into three main types: topical treatments, light therapy and systemic medications. Such topical treatments include, but are not limited to, corticosteroids, vitamin D analogues, anthralin, retinoids, calcineurin inhibitors, salicylic acid, coal tar, and moisturizers. Such light therapies include, but are not limited to, sunlight, UVB phototherapy, narrow band UVB phototherapy, Goeckerman therapy, psoralen plus ultraviolet A (PUVA) and exclimar laser. Such systemic medications include, but are not limited to, retinoids, methotrexate, cyclosporine, thioguanine, or hydroxyurea. Additionally, some psoriasis treatments include alternative medicines including, but not limited to, aloe vera, fish oil, and Oregon grape.

Prognostic Methods and Methods of Treatment

In addition to the utilities described above, the biomarker or combination of biomarkers of the disclosure are useful in determining efficacy of a treatment for psoriasis. The phrase "treating psoriasis" includes ameliorating psoriasis and encompasses treating or ameliorating any of the symptoms associated with psoriasis.

In some aspects, it is useful to select subjects for treatment based on biomarker expression level. Also, in some aspects, it is useful to select subjects for treatment based on biomarker expression level along with the presence or absence of a variety of clinical parameters, such as PASI score, as discussed herein. Accordingly, the disclosure provides in one aspect a method of treating psoriasis in a subject suffering from psoriasis, wherein the method comprises the steps of measuring a level of a biomarker or a combination of biomarkers in a biological sample isolated from the subject, and wherein an increased or decreased level of the biomarker or combination of biomarkers present in the biological sample compared to a control level indicates a probability of successfully treating the subject with an anti-TNF agent, and administering an effective amount of a treatment comprising an anti-TNF agent.

In some embodiments, methods are provided for prognosing responsiveness to an anti-TNF agent in treatment of psoriasis in a subject and for treating psoriasis in a subject with an anti-TNF agent after it is determined or predicted that the subject will favorably respond to treatment with the anti-TNF agent.

The disclosure provides a method for prognosing responsiveness to an anti-TNF agent in treatment of psoriasis in a subject, the method comprising measuring a level of at least one biomarker in a biological sample of uninvolved skin isolated from the subject prior to treatment with the anti-TNF agent, wherein the at least one biomarker is ubiquitin specific protease 18 (USP18); keratin, type II cytoskeletal 2 epidermal (KRT2); interleukin 4 receptor (IL4R); sex-determining region Y-box transcription factor 5 (SOX5); interferon induced with helicase C domain 1 (IFIH1); or a combination of any two or more of the aforementioned biomarkers, and comparing the level with a control level, wherein the control level is the mean level of the biomarker in uninvolved skin in a population of subjects suffering from psoriasis prior to treatment with the anti-TNF agent, wherein when the level of USP18, ILR4, and/or IFIH1 in the subject is increased relative to the control level of the biomarker, the subject is predicted to be responsive to treatment with the anti-TNF agent, wherein when the level of KRT2 and/or SOX5 in the subject is decreased relative to the control level of the biomarker, the subject is predicted to be responsive to treatment with the anti-TNF agent, wherein when the level of USP18, ILR4, and/or IFIH1 in the subject is not increased relative to the control level of the biomarker, the subject is predicted to be non-responsive to treatment with the anti-TNF agent, and/or wherein when the level of KRT2 and/or SOX5 in the subject is not decreased relative to the control level of the biomarker, the subject is predicted to be non-responsive to treatment with the anti-TNF agent.

The disclosure provides a method for treating psoriasis in a subject, the method comprising measuring a level of at least one biomarker in a biological sample of uninvolved skin isolated from the subject prior to treatment with an anti-TNF agent, wherein the at least one biomarker is USP18 and the level of USP18 is increased relative to a control level; wherein the at least one biomarker is KRT2 and the level of KRT2 is decreased relative to a control level; wherein the at least one biomarker is IL4R and the level of IL4R is increased relative to a control level; wherein the at least one biomarker is SOX5 and the level of SOX5 is decreased relative to a control level; wherein the at least one biomarker is IFIH1 and the level of IFIH1 is increased relative to a control level; or wherein the at least one biomarker is a combination of any two or more of the aforementioned biomarkers; wherein the increased or decreased level of the biomarker in the subject relative to the control level predicts that the subject will be responsive to treatment with the anti-TNF agent, and wherein the control level is the mean level of the biomarker in uninvolved skin in a population of subjects suffering from psoriasis prior to treatment with the anti-TNF agent; and administering an effective amount of an anti-TNF agent to the subject predicted to be responsive to treatment.

In cases in which a method comprises combination of steps, each and every combination or sub-combination of the steps is encompassed within the scope of the disclosure, unless otherwise noted herein.

In regard to any of the methods provided, the steps of the method may occur simultaneously or sequentially. When the steps of the method occur sequentially, the steps may occur in any order, unless noted otherwise.

Kits

As an additional aspect, the disclosure includes kits which comprise reagents packaged in a manner which facilitates their use for measuring a biomarker in a biological sample from a subject suffering from psoriasis. In some variations, such reagents are packaged together. In some variations, the kit further includes an analysis tool for evaluating the probability that the subject will favorably respond to an anti-TNF therapy after taking a measurement of at least one biomarker from a biological sample from the subject.

In one embodiment, the disclosure pertains to a kit for assaying a sample from a subject to determine the likelihood that the patient will positively respond to an anti-TNF therapy, wherein the kit comprises reagents necessary for selectively detecting the relative level of the biomarker or a combination of biomarkers in the subject and comparing them to a control. In certain embodiments, the biomarker is USP18, KRT2, IL4R, SOX5, or IFIH1. In certain embodiments, the kit comprises one or more reagents for detecting and/or measuring the relative expression level of USP18, KRT2, IL4R, SOX5, or IFIH1, or a combination of any one or more thereof in a sample from a subject suffering from psoriasis.

In a specific embodiment, the kits of the disclosure each contain an apparatus for collecting a biological sample from a subject and reagents for measuring the level of biomarker in a biological sample. In a further aspect, the kit comprises optional instructions included in the package that describes use of the reagents packaged in the kit for practicing the method.

In a further aspect of the present invention, a pharmaceutical pack (kit) is provided, the pack comprising an anti-TNF agent and a set of instructions for administration of the anti-TNF agent to a subject diagnostically tested and determined to be a subject who will favorably respond to treatment of their psoriasis with an anti-TNF agent. The anti-TNF agent can be any of the anti-TNF agents described herein. In exemplary aspects, the anti-TNF agent is etanercept.

In some embodiments, the kit further comprises a set of instructions for using the reagents comprising the kit. In certain embodiments, the kit further comprises a collection of data comprising correlation data between the biomarker level and the probability that the subject will favorably respond to treatment with the anti-TNF agent. In some aspects, therefore, the kit provides a means for measuring the relative level of the biomarker or biomarkers at day 0 and determining the relative increase or decrease in the level of the biomarker from a sample from the subject compared to the control level, i.e., the mean level of the biomarker at day 0 from the population of control subjects.

Each publication, patent application, patent, and other reference cited herein is incorporated by reference in its entirety to the extent that it is not inconsistent with the present disclosure.

Recitation of ranges of values herein are merely intended to serve as a shorthand method for referring individually to each separate value falling within the range and each endpoint, unless otherwise indicated herein, and each separate value and endpoint is incorporated into the specification as if it were individually recited herein.

All methods described herein are performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Additional aspects and details of the disclosure will be apparent from the following examples, which are intended to be illustrative rather than limiting.

Example 1

Materials and Methods

Patient Cohort

Patients with moderate-to-severe chronic plaque psoriasis for longer than 6 months were enrolled on an open-label 50 mg biweekly etanercept treatment for three months. Study protocols were approved by the University of Michigan Institutional Review Board, and were carried out in accordance with Good Clinical Practice requirements and the Declaration of Helsinki. Informed consent was acquired from all participants. Patients were evaluated at baseline, and biopsy obtained under local anesthesia (lidocaine 1:10,000 epinephrine) from both uninvolved and lesional skin at baseline, and from lesional skin only at weeks 2, 6 and 12. Patients had full clinical assessment at 2, 6 and 12 weeks by a dermatologist and body-surface area, physician-global assessment and Psoriasis Area and Severity Index (PASI) were recorded. The study was registered on clinicaltrials.gov (NCT01971346).

RNA-seq Processing 50 bp single-ended reads were generated from 210 RNA-seq samples from 46 patients. For each sequence file, trimmomatic was used to conduct adapter trimming (Bolger et al., Bioinformatics 2014; 30(15):2114-20), and STAR (Dobin et al., Bioinformatics. 2013; 29(1):15-21) was used for aligning the reads to human genome b37. HTSeq was employed for expression level quantification (Anders et al., Bioinformatics 2015; 31(2):166-9), and only uniquely mapped reads were utilized. From 46 patients: one patient was removed due to drop out; two patients were removed because they did not have baseline (week 0) biopsy samples, leaving 43 patients and 206 RNA-seq samples for the subsequent analysis. One patient's last visit was conducted on week 15, and the results were grouped to the week 12 data for all other patients when conducting the analysis. 28,182 genes were detected with on average>=1 read/sample, and we applied DEseq2 was applied for read normalization (Love et al., Genome Biol. 2014; 15(12):550). Principal component analysis was conducted using all genes after applying inverse normalization for the DESeq2 normalized data.

Associating RNA-seq Expression with Clinical Response

Each gene expression profile, from baseline uninvolved or lesional skin samples, was correlated against change in psoriasis-area-and severity index (PASI), body surface area (BSA), and static Physician Global Assessment (sPGA) in each of the three follow-up visits. Age, gender, and baseline BMI of the patients were adjusted, and evaluated as both percent (%) as well as absolute (i.e. delta) disease improvement referencing the week 0 values. False Discovery Rate 0% was declared significant for association. Differential expression analyses (i.e. comparing uninvolved vs lesional skin at baseline; comparing lesional skin at baseline versus subsequent visit) were conducted using DESeq2 negative binomial distribution, and FDR<=10% and |log2Fold Change|>=1 were used as criteria to declare significant genes.

Comparison Against Cytokine Signatures in Keratinocytes

The procedures for identifying the cytokine signatures in keratinocytes were described previously [Tsoi et al., J. Invest. Dermatol. 2019 July; 139(7):1480-1489. doi: 10.1016/j.jid.2018.12.018. Epub 2019 Jan. 11. PMID: 30641038]. Briefly, 50 normal human keratinocyte samples from 50 different healthy adults were obtained. Keratinocytes were grown in a 12-well plate in 154 CF medium (Thermo Fisher #M154CF500) with human keratinocyte growth supplement (Thermo Fisher #S0015). Keratinocytes were grown to confluency at which time the complete medium (with supplements) was replaced by basal 154 CF medium (without supplements). Cells were then stimulated with cytokines (IL-4, IL-13, IFN-α, IFN-γ, TNF-α, and IL-17A (R&D Systems)), each provided individually at 10 ng/ml concentration. After 8 hrs, cells were harvested and RNA was isolated using RNeasy Plus Mini kit (Qiagen #74136). RNA was analyzed by RNA Nano Chips (Agilent Technologies) and sequenced (Sarkar et al., Ann Rheum Dis. 2018, 77:1653-1664). The top 1,000 genes were extracted with their baseline expression profiles showing the strongest correlations with future absolute PASI improvement in each of the three follow-up visits, and used in a hypergeometric test to compare against cytokine signatures to understand their molecular basis.

Predicting Drug Response

Each patient from the cohort was assigned a TNF or IFN score based on their baseline expression profiles in uninvolved skin: for each gene i induced by TNF/IFN in keratinocytes. The relative expression of that gene in patient p was determined by referencing the median value across samples: $rp^i = gp^i/\mathrm{median}(g^i)$, where g is the normalized expression. The TNF or IFN score for patient p was then defined as the upper quartile of the $r^p$ value across all genes induced by TNF or IFN, respectively. To model the week 12 PASI response, baseline uninvolved skin expression profiles for the genes induced by TNF/Type I IFN by keratinocyte experiments (as described herein above) were utilized. Principal components were used to reduce the data dimension. Logistic regression was applied to model the drug responses at week 12 using the PASI 75 criteria, using leave-one-out to ensure the robustness upon model evaluation (i.e. principal component analysis and regression modeling were performed only on the training data). A 75% reduction in the PASI score (PASI 75) is the current benchmark of primary endpoints for most clinical trials of psoriasis. The area under the receiver operative characteristic (AUROC) was computed for PASI 75 using different numbers of principal components. Finally, to further assess the potential clinical implication, the precision (proportion of true positives among the predicted PASI75) and recall (proportion of actual PASI75 predicted), as functions of the proportion of top samples predicted from the model, was measured.

Immunohistochemistry

Formalin fixed, paraffin-embedded tissue slides obtained from patients with psoriasis and skin samples from healthy people not suffering from psoriasis, i.e., healthy or normal controls, were heated for 30 min at 60° C., rehydrated, and epitope retrieved with Tris-EDTA, pH 6. Slides were blocked, incubated with a USP18 primary antibody (1:100; LS-B1182-50; Lifespan Bioscience) overnight at 4° C. Slides were then washed with PBS and incubated with a biotinylated secondary antibody (biotinylated goat anti-rabbit IgG Antibody; BA1000; Vector Laboratories) for 30 min at room temperature, and then incubated with fluorochrome-conjugated streptavidin for 10 min at room temperature. Slides were prepared in mounting medium with 4',6-diamidino-2-phenylindole (DAPI) (VECTASHIELD Antifade Mounting Medium with DAPI, H-1200, VECTOR). Images were acquired using a Zeiss Axioskop 2 microscope and analyzed by SPOT software 5.1. Images presented were representative of at least three experiments.

RNAi Depletion, RNA Extraction, qRT-PCR

Upon reaching semi-confluence, the culture medium of keratinocytes was changed by Accell Delivery Media (B-005000, Dharmacon) with 1 μM Accell siRNA targeting USP18 (E-004236-00-0005, Dharmacon). After 48 h, cells were stimulated with IFN-α (10 ng/ml, 14276, R&D Systems), TNF-α (10 ng/ml, 210-TA, R&D Systems), IL-17A (20 ng/ml, 7955-IL, R&D Systems), or IFN-γ (10 ng/ml, 285-IF, R&D Systems) for another 24 h. RNA was isolated from cells using RNeasy plus kit (74136, Qiagen). QRT-PCR was performed on a 7900HT Fast Real-time PCR system (Applied Biosystems) with TaqMan Universal PCR Master Mix (ThermoFisher 4304437). Primers (ThermoFisher Scientific) used in this study were: USP18, Hs00276441_m1; IL36G, Hs00219742_m1; DEFB4, Hs00175474_m1; MX1, Hs00895608_m1; OASL, Hs00984387_m1; IRF7, Hs01014809_g1; IFNK, Hs00737883_m1 (ThermoFisher Scientific).

Example 2

RNA-seq to Profile the Trajectory of Transcriptome for Patients Initiated on Etanercept Therapy 46 psoriatic patients were enrolled for this study (FIG. 1A). Each patient was treated with etanercept (trade name Enbrel or Benepali), twice weekly with 50 mg. Prior to initiation (baseline/week 0), demographic information (age, sex) and other clinical information, including PASI score, body surface area (BSA), and sPGA were collected. Skin punch biopsies were performed at baseline on uninvolved and lesional skin for transcriptome profiling using RNA-seq, and additional lesional samples were obtained at the time of follow-up on week 2, week 6, and week 12, along with clinical assessment. Follow-up data on 42 patients was obtained (i.e. with transcriptomic data from both baseline and at least one of the follow-up visits), and a total of 36 patients completed the study with RNA-seq and clinical data available at both baseline and at the week 12 visit.

Figure 1C:
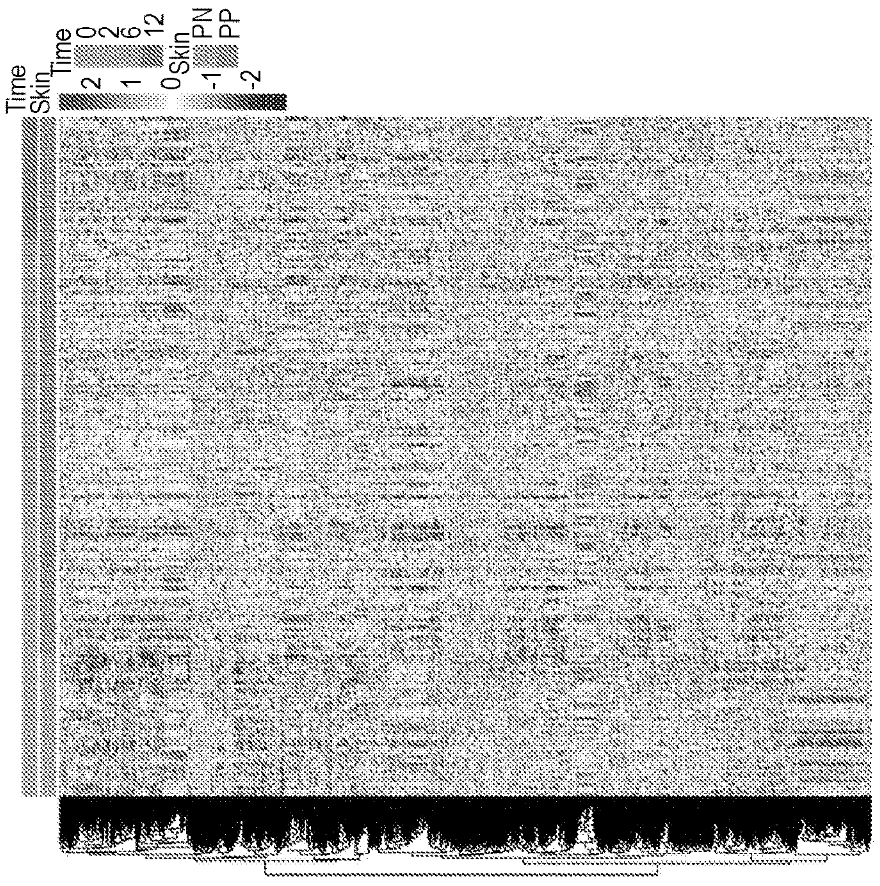
Figure 1B:
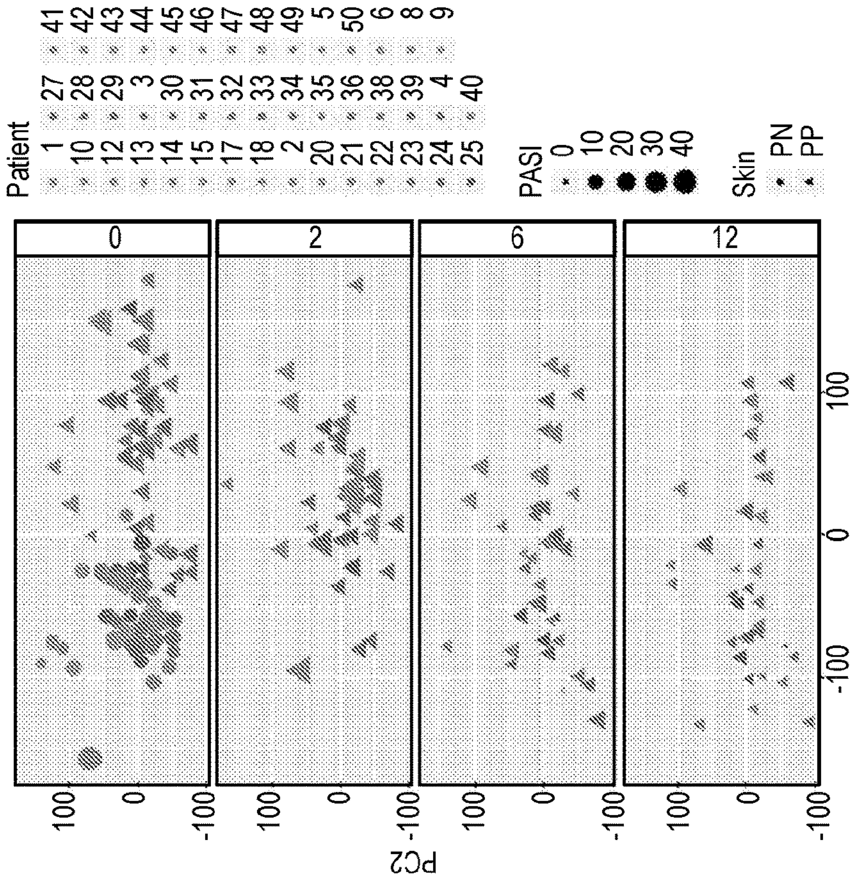
Figure 6:
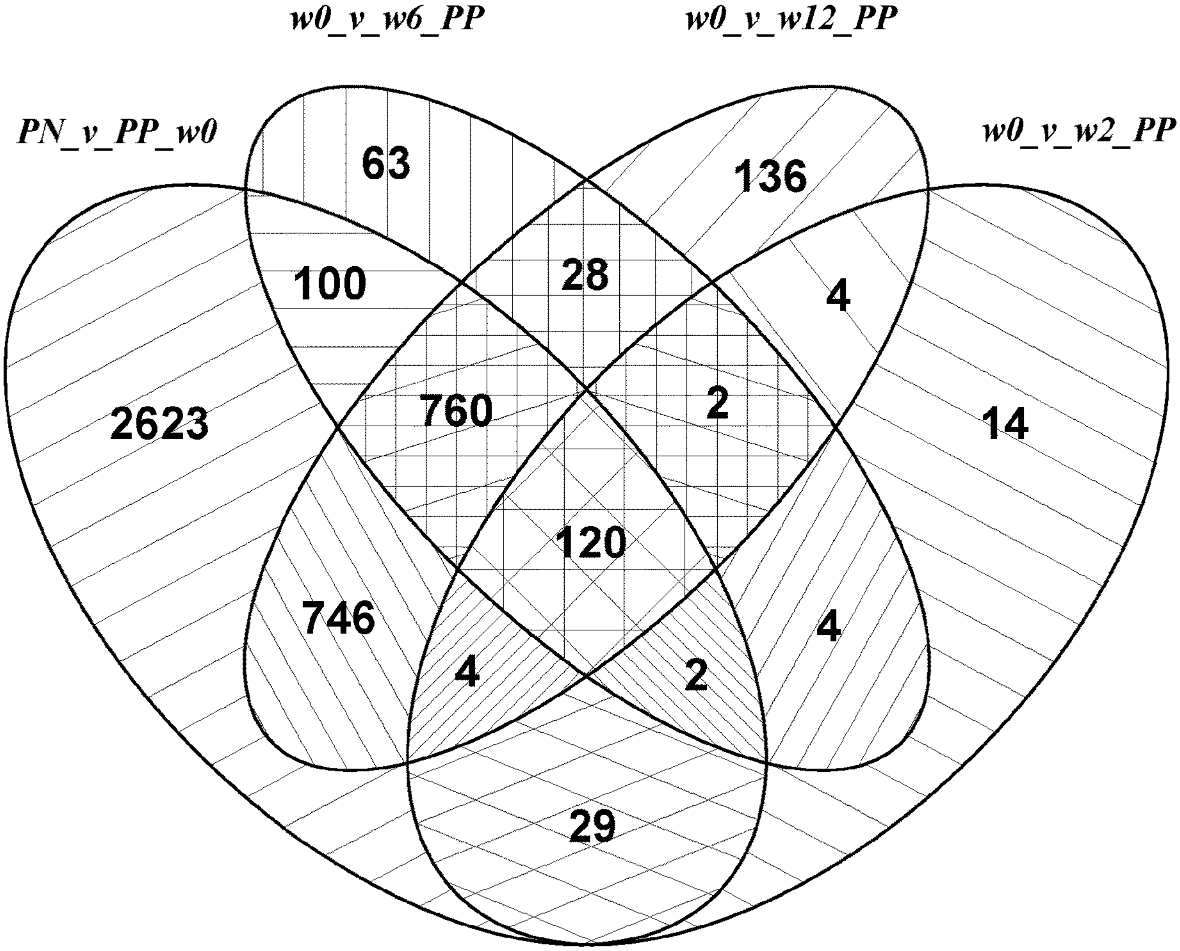
FIG. 6 is a Venn diagram illustrating the overlap between differential expressed genes identified in different comparisons. PN: non-lesional skin; PP: lesional skin.

A total of 210 RNA-seq experiments were performed on the 46 patients in the cohort. By using principal component analysis (PCA), changes of the transcriptomes were tracked over the treatment course (FIG. 1B). As expected, PCA separated uninvolved and lesional skin at baseline, but during the treatment period, the largest principal component (i.e., PC1) of lesional skin changed over time such that by week 12 it overlapped, in a proportion of the cohort, with that of uninvolved skin at baseline. However, some patients still had PC1 values that remained at baseline level by week 12, despite improvement in PASI. Notably, the former group tended to have a lower PASI score than the latter group at week 12 (lower panel in FIG. 1B). Changes over time were further investigated at the gene expression level to determine how the expression profiles changed during the 12-week treatment period (FIG. 1C): Similar to the PCA results , there was a sharp contrast between uninvolved and lesional skin at baseline, but the contrast decreased (or became less apparent) as treatment with etanercept proceeded. Indeed, when comparing gene expression levels in baseline lesional skin with that from follow-up visits, a gradual increase in the number of differentially expressed transcripts was observed (see Table 2 below), and restoration towards gene expression levels in uninvolved skin at baseline (FIG. 6) was observed.

Nevertheless, heterogeneity was observed among patients' transcriptomic responses at week 12, concordant with the clinical variations (Leonardi et al., N Engl J Med. 2003; 349(21):2014-22; Zaba et al., J Allergy Clin Immunol. 2009; 124(5):1022-10 e1-395.)).

TABLE 2

Number of differentially expressed genes when comparing the lesional skin (PP) from baseline versus that from follow-up visits.

| PP week 0 versus: | Up-regulated genes | Down-regulated genes | Total Differential expressed genes |
|---|---|---|---|
| Week 2 | 47 | 132 | 179 |
| Week 6 | 547 | 532 | 1,079 |
| Week 12 | 1,004 | 796 | 1,800 |

Example 3

Expression Profiles at Baseline Uninvolved Skin are Associated with PASI Improvement The associations between baseline expression profiles and clinical presentation were examined. The expression level (from uninvolved or lesional skin) of each gene at week 0 was correlated with the change in PASI, BSA, and/or sPGA in each of the three follow-up visits. Both percent (%) as well as absolute (i.e., delta) disease improvement were evaluated, referencing the week 0 values.

Surprisingly, significant associations between gene profiles could be identified only in baseline uninvolved skin, rather than lesional skin, versus PASI improvement from at least one of the follow-up visits. When using percent change as measure, there were 198 genes with their week 0 expression profiles significantly (FDR<=10%) associated with week 12 PASI improvement. When using absolute change as measure, there were 192 genes at week 6 and 391 genes at week 12 with their baseline expression profiles significantly associated with week PASI improvement. No significant results for associations against BSA and sPGA change were detectable.

Figures 2A, 2B, 2C, 2D, 2E, 2F:
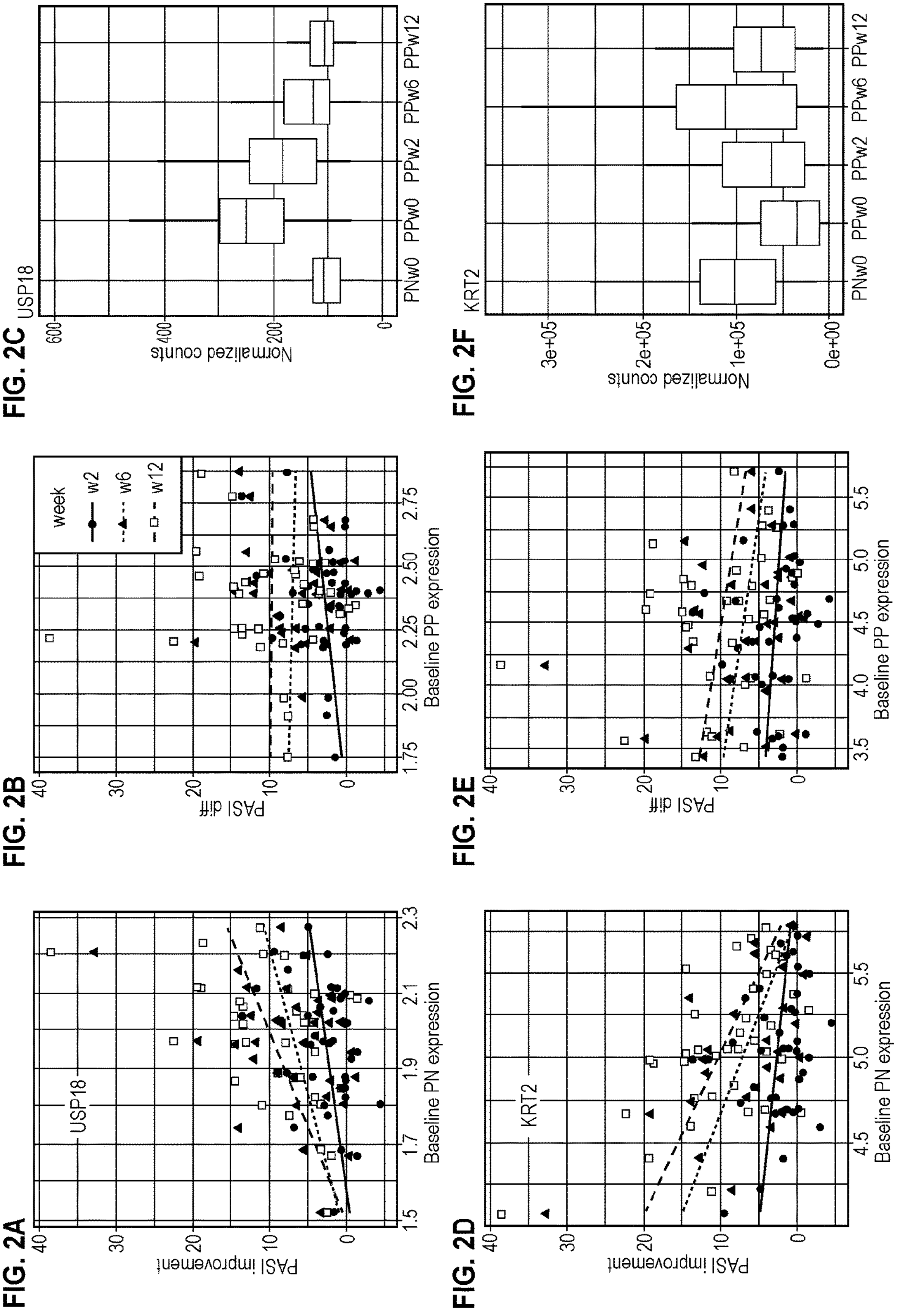
FIG. 2A-E depicts the associations between PASI improvement and baseline expression and expression of USP18 and KRT2 over time. PASI improvement (y-axis) was plotted against baseline expression of USP18 (FIG. 2A-B) and KRT2 (FIG. 2D-E) in uninvolved (FIGS. 2A and 2D) and lesional skin (FIGS. 2B and 2E). The boxplots for normalized expression levels of USP18 (FIG. 2C) and KRT2 (FIG. 2F) under different skin and time points during the course of treatment are shown. Although the gene's (i.e., USP18 and KRT2) associations with PASI improvement at week 2 and week 6 were not significant, the direction of correlations was consistent (FIGS. 2A and 2D); interestingly, these associations were not observed when using baseline expression levels in lesional skin (FIGS. 2B and 2E). The expression levels of USP18 and KRT2 genes in lesional skin gradually "restored" towards expression levels in uninvolved skin over time (FIGS. 2C and 2F). These results indicate that both USP18 and KRT2 are dysregulated in psoriatic skin but can be "restored" to uninvolved skin levels by etanercept treatment, and their relative expression levels in uninvolved skin prior to treatment are associated with future PASI improvement and therefore are useful in predicting therapeutic response to an anti-TNF agent.

Among the significant genes with their baseline expressions associating with PASI improvement at week 12, 105 of them overlapped between the percent and absolute measures. USP18, an ubiquitin specific peptidase, and KRT2, a type I cytokeratin, are two prominent examples with expression in uninvolved skin at baseline showing significant association with PASI improvement in follow-up visit (FIG. 2A-F):

USP18 was significantly up-regulated in lesional skin at baseline (fold change, FC=2.5; $p=1\times10^{-26}$), and its expression in uninvolved skin at baseline was positively correlated with absolute PASI improvement at week 12 ($p=9.8\times10^{-4}$; 20% increase from mean expression level has on average 2.3 PASI improvement after adjusting for age, gender, and BMI); KRT2 was significantly down-regulated in lesional skin at baseline (FC=0.32; $p=1.3\times10^{-6}$) and its expression in uninvolved skin at week 0 was inversely correlated with both the absolute ($p=1.4\times10^{-5}$; 20% decrease from mean expression level has on average 0.99 PASI improvement after adjusting for age, gender, and BMI) and percent ($p=5.4\times10^{-4}$) PASI improvement at week 12. Although their associations with PASI improvement at week 2 and week 6 were not significant, the direction of correlations is consistent (FIGS. 2A and 2D). Interestingly, these associations were not observed when using baseline expression levels in lesional skin (FIGS. 2B and 2D). Furthermore, the expression levels of these two genes in lesional skin gradually "restored" towards expression levels in uninvolved skin over time (FIGS. 2C and 2F). These results indicate that both USP18 and KRT2 are dysregulated in psoriatic skin but can be "restored" to uninvolved skin levels by etanercept treatment, and their expression level in uninvolved skin prior to treatment are associated with future PASI improvement.

Figures 3A, 3B:
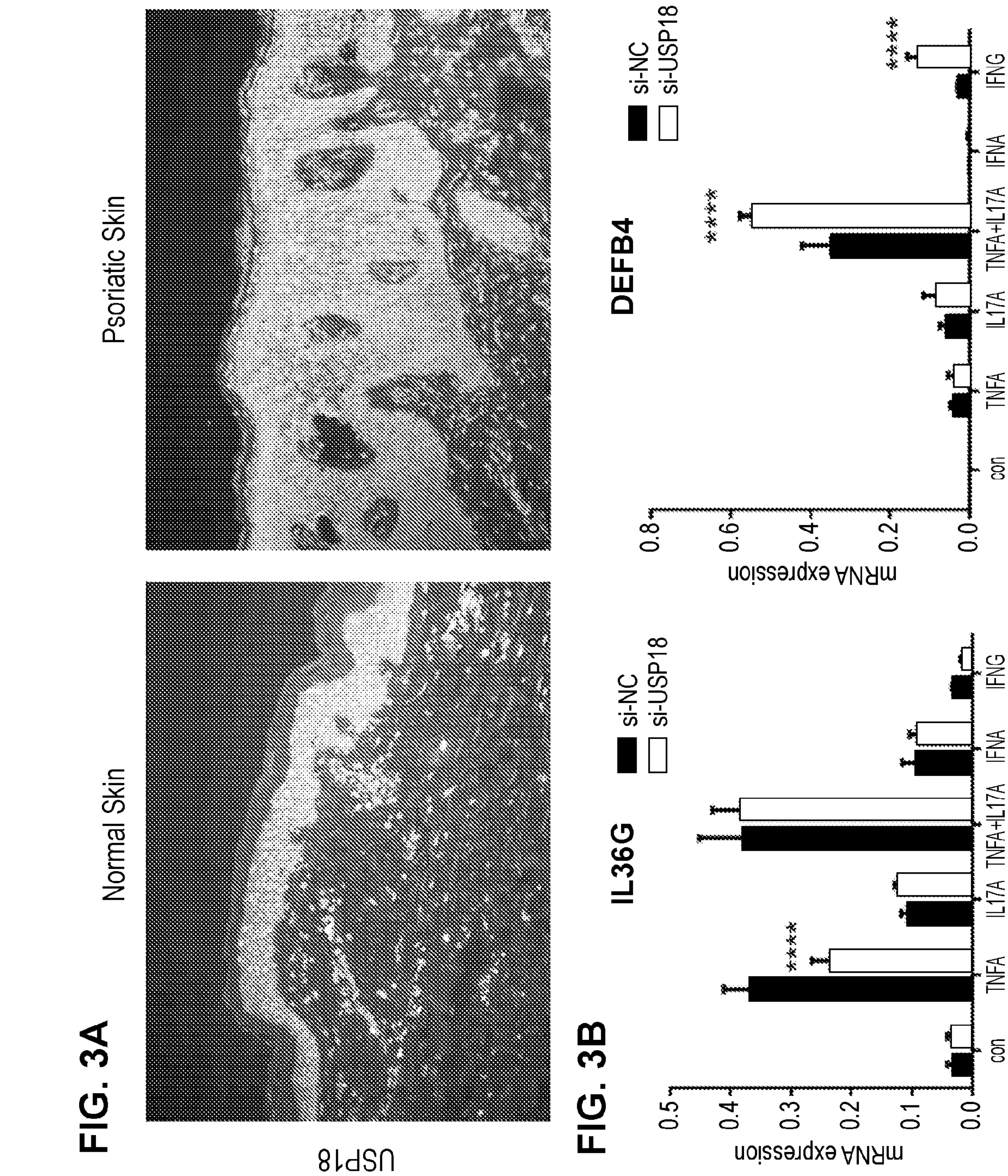
FIG. 3A-H shows USP18 as a modulator for IFN/TNF response.
Figure 3C:
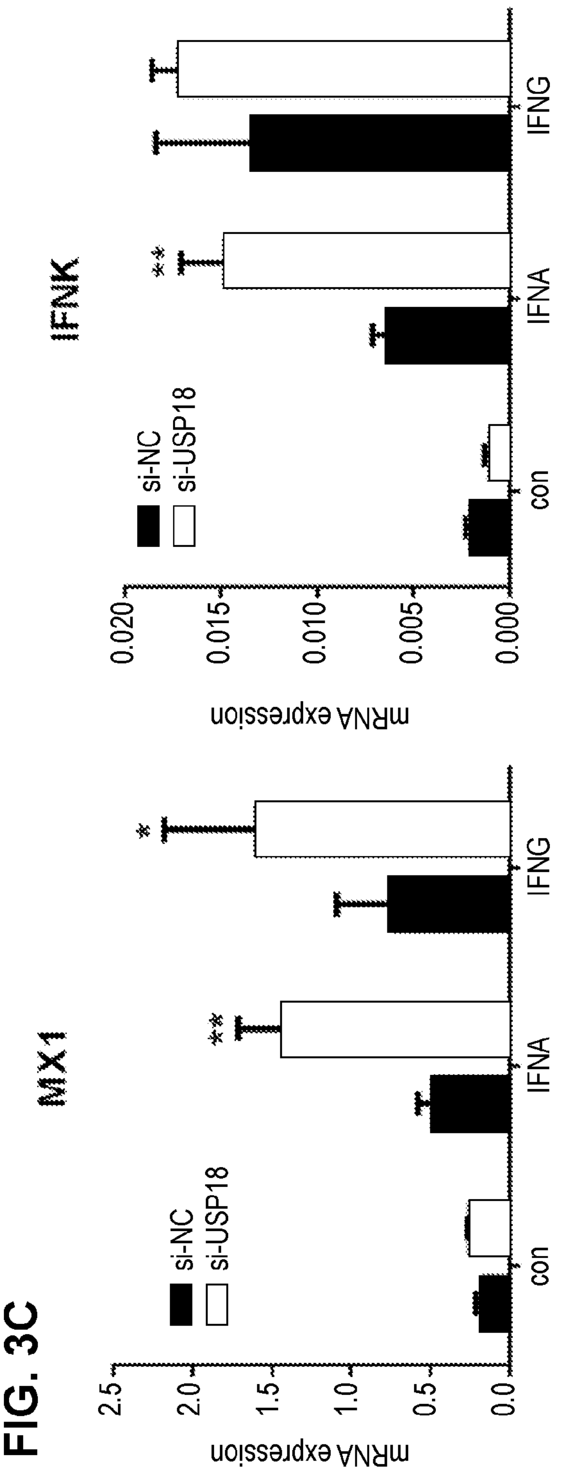
Figure 3D:
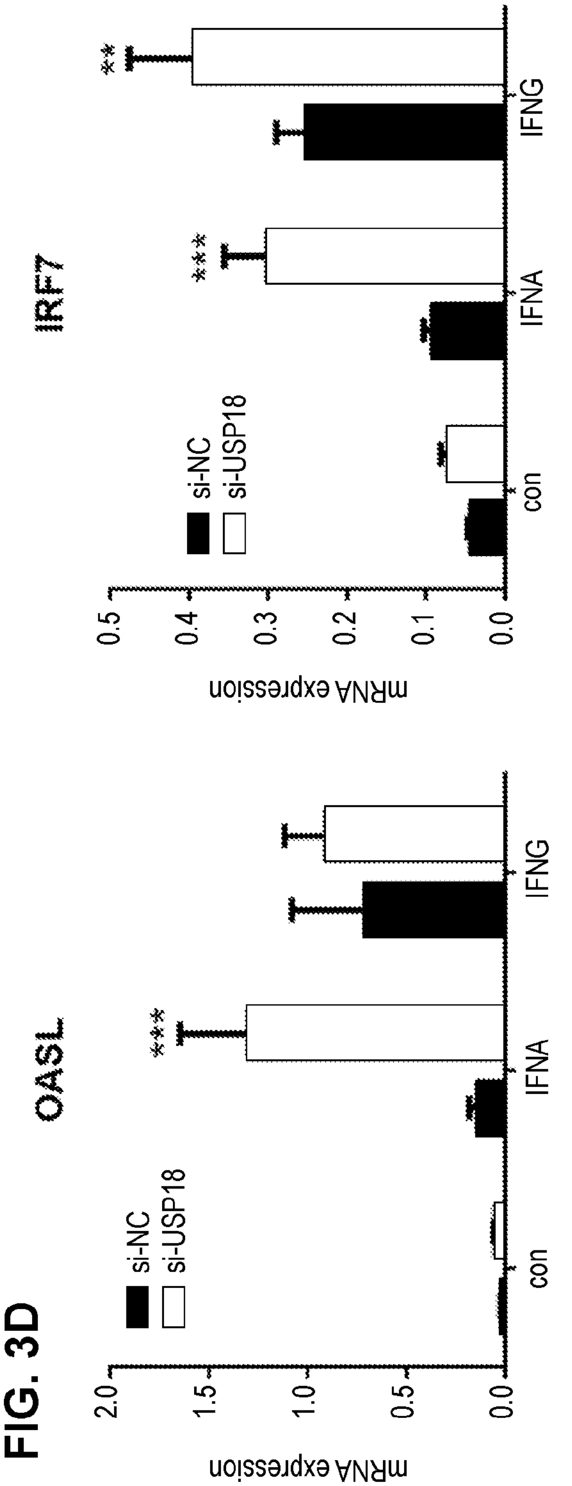
Figure 3E:
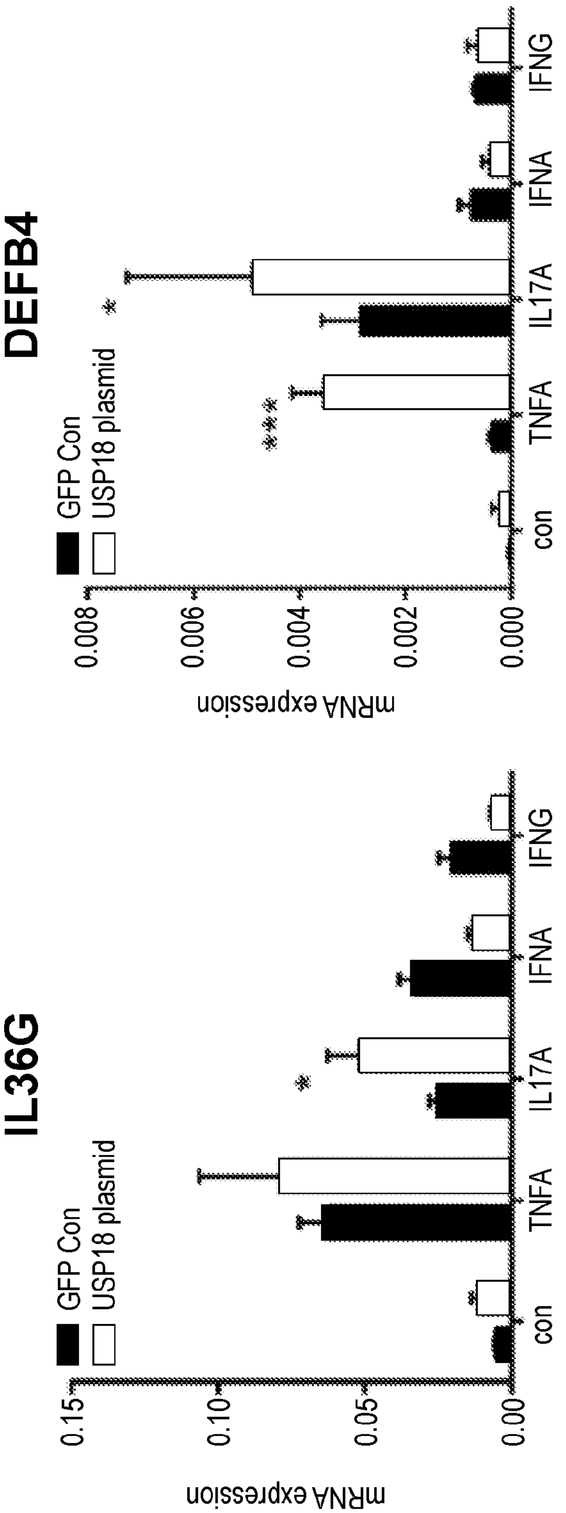
Figure 3F:
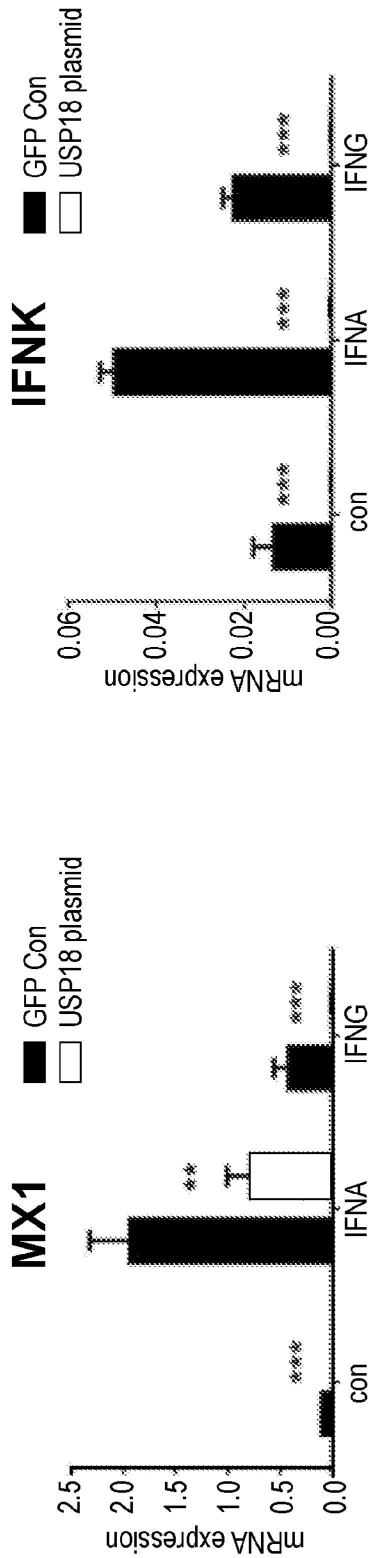
Figure 3G:
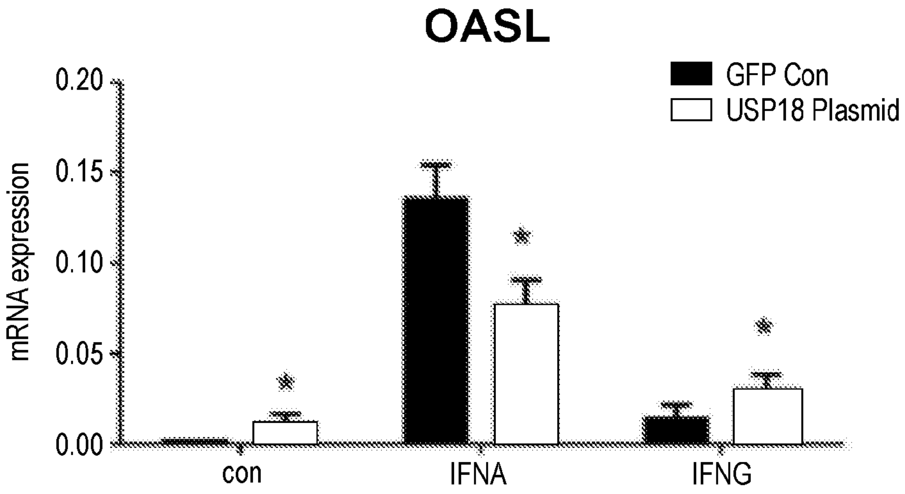
Figure 3H:
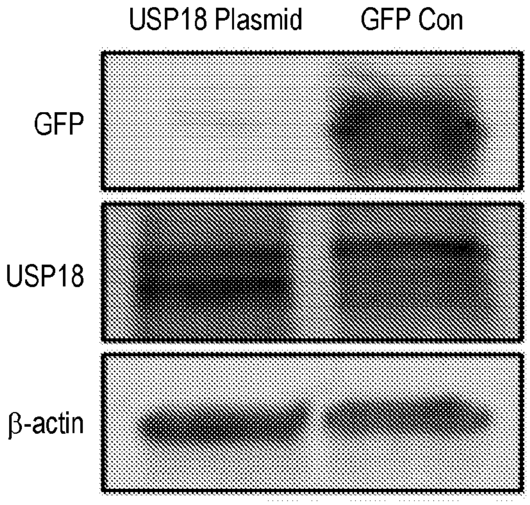
Figure 7:
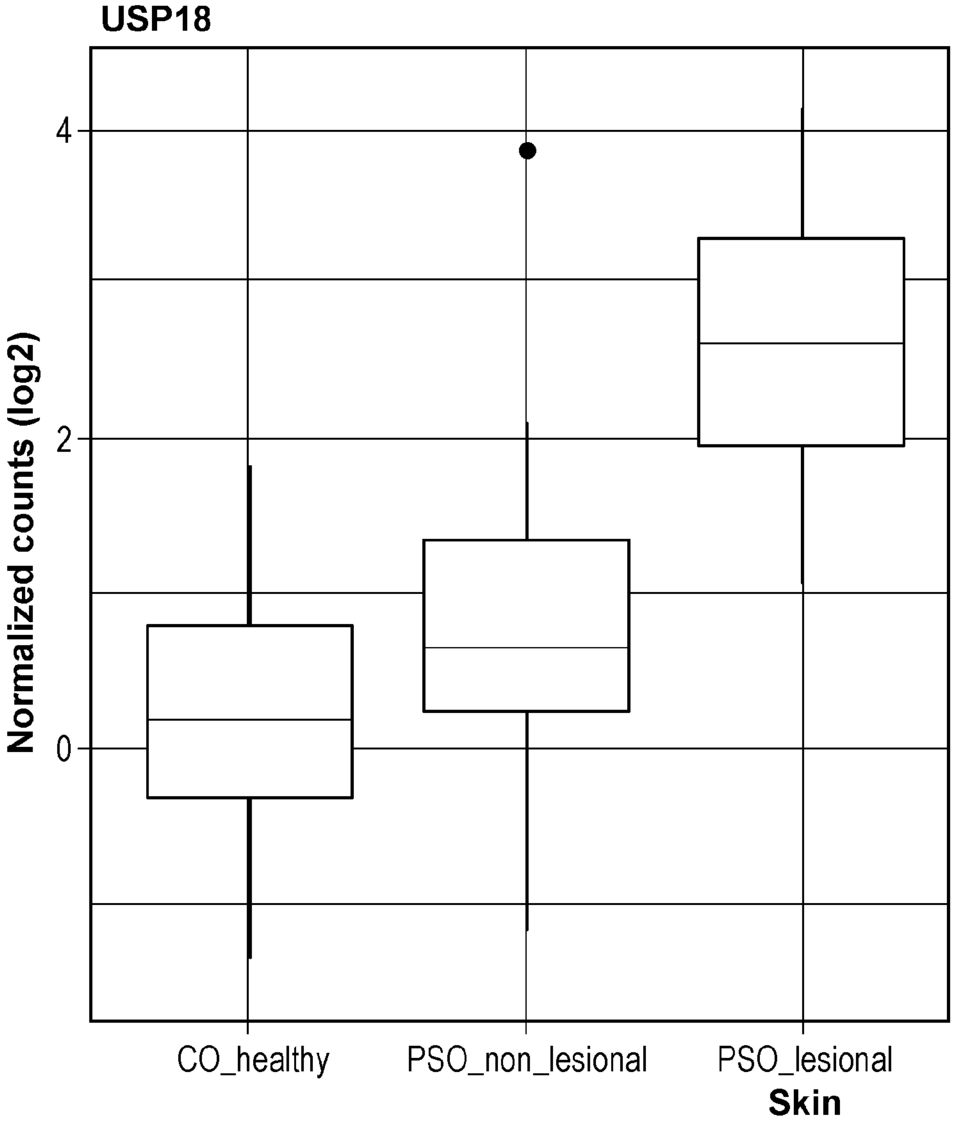
FIG. 7 shows normalized expression levels of USP18 in control, uninvolved, and lesional skin from an independent psoriasis transcriptomic cohort.

Several functional assays were carried out to better understand the potential role of USP18 in TNF responses. First, an independent transcriptomic cohort recently conducted was used to validate the up-regulation of USP18 in lesional skin (FIG. 7). Interestingly, the expression level of USP18 was found to be marginally up-regulated in uninvolved skin when compared with normal skin (FC=1.5; $p=1.2\times10^{-2}$). USP18 is also positively correlated with other psoriasis cytokines (IL23A and IL36G) in lesional skin ($p=6.3\times10^{-5}$ and $p=8.3\times10^{-7}$, respectively). By using immunostaining (FIG. 3A), the distribution of USP18 proteins in both uninvolved and lesional psoriatic skin was observed, confirming its expression in the epidermal layer. Small inhibitory RNA (siRNA) was used to knockdown the expression of USP18 in keratinocytes and evaluate the impact on TNF/interferon (IFN) responses. Significantly, the effective knock-down of USP18 had an effect on both TNF and IFN stimulations (FIG. 3B-D). Upon TNF stimulation, USP18 knock-down tended to suppress IL36G mRNA expression but tended to induce DEFB4 mRNA expression (during TNF+IL17 stimulation). Upon IFN stimulation, USP18 knock-down promoted greater expression of IFN-response genes, including MX1, IFNK, OASL, and IRF7. Conversely, USP18 overexpression (FIG. 3E-G) decreased type I and type II IFN responses (FIG. 3E-G) but enhanced IL-17A induced effect on IL36G and TNF-induced effect on DEFB4 (FIG. 3E). These results suggest that USP18 has an inhibitory effect on IFN response, while facilitating some TNF responses (i.e., IL36G mRNA expression).

Because IFN and TNF have been thought to have counter-regulatory roles in psoriasis (Conrad et al., Nat Commun. 2018; 9(1):25), a lower USP18 expression level, in some aspects, may be helpful in promoting a greater IFN response and, thus, lower dependence on TNF, in agreement with the observation that USP18 has a positive correlation with PASI improvement during the course of etanercept treatment.

Example 4

Figure 4A:
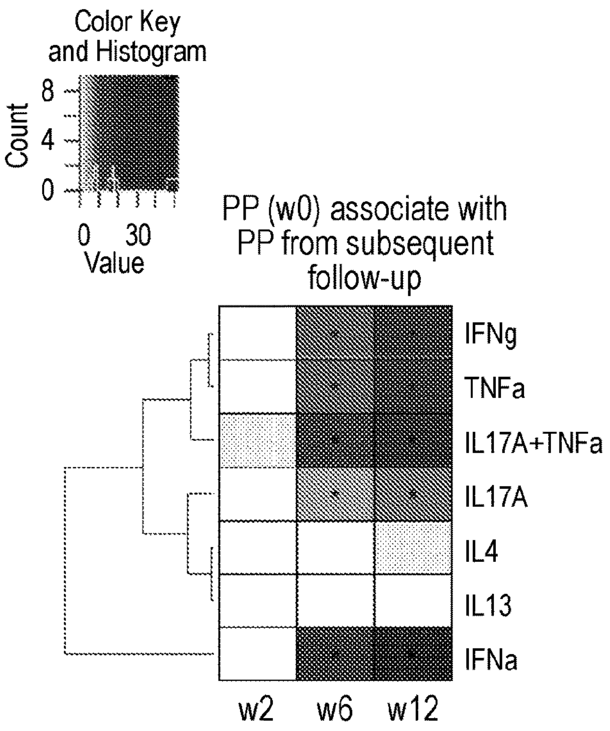
FIG. 4A-C demonstrates the enrichment of different cytokine signatures in different association comparisons.

Integrative Approach to Provide Biological and Clinical Implications using Uninvolved Skin An integrative approach was used to understand how RNA-seq results could be used to provide biological and clinical implications for etanercept treatment in psoriasis. Results with in vitro experiments studying the effect of different cytokine stimulations in keratinocytes were first analyzed. Among the genes showing the strongest differential expression (upregulation and downregulation) in lesional skin between baseline and subsequent follow-up visits, significant (FDR (or log fold change) 0%) enrichment of IFN, TNF, and IL17 signatures (FIG. 4A) were observed, concordant with the etanercept's TNF inhibitory effect and its associated negative regulation on Th17 response (Krueger et al., J. Amer. Acad. Derm. 2006;54(3 Suppl 2):S112-9; Zaba et al., J Allergy Clin Immunol. 2009;124 (5):1022-10 e1-395).

Figure 4B:
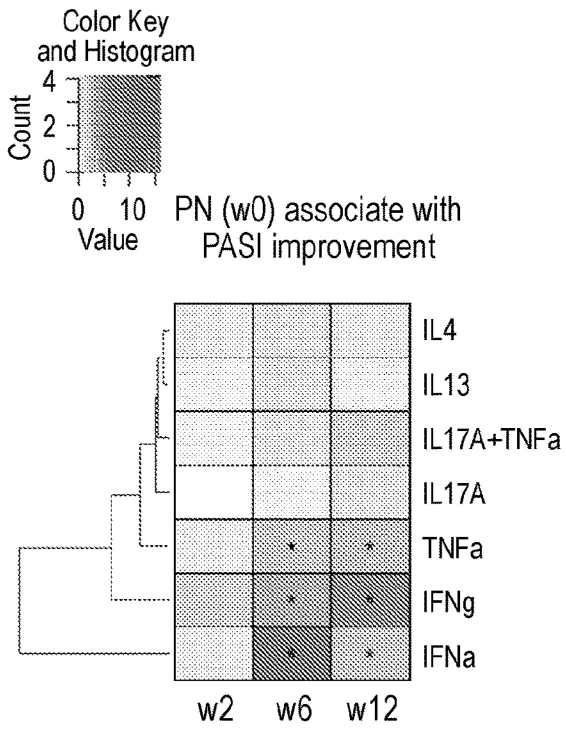
Figure 4C:
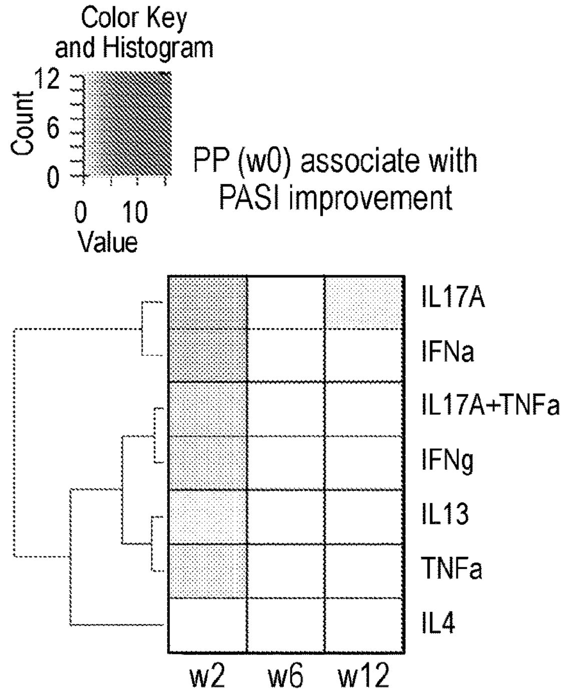
Figure 8:
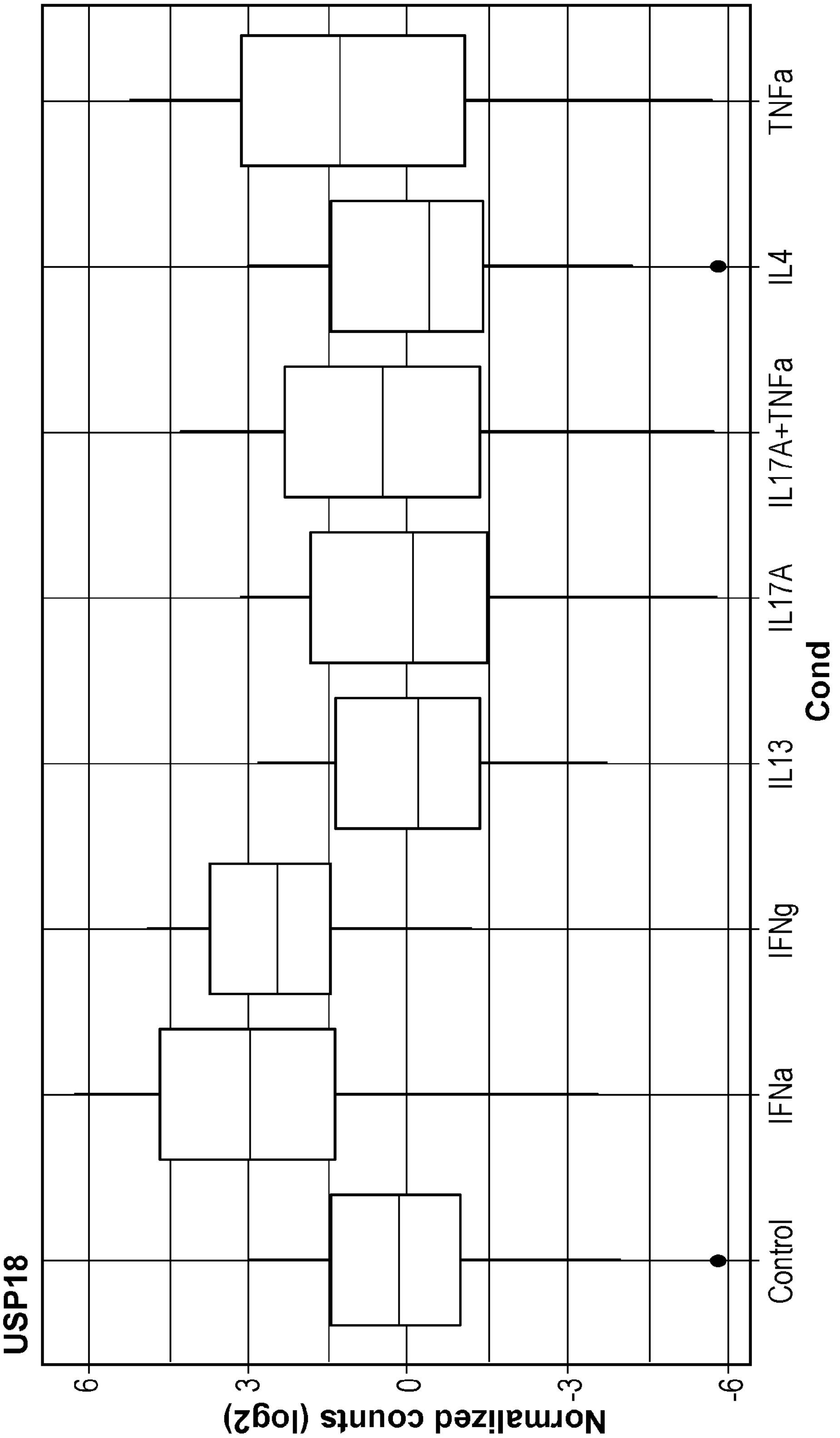
FIG. 8 shows normalized expression levels of USP18 under different cytokine stimulations in keratinocytes.

Next, the top 1,000 genes with their baseline expression profiles showing the strongest correlations with future absolute PASI improvement in each of the three follow-up visits were extracted, and compared against type I IFN, TNF and IL-17A keratinocytes cytokine signatures to understand their molecular basis. Strikingly, it was found that significant enrichment for TNF and Type I IFN signatures for week 0 uninvolved skin gene expression profiles have the strongest correlations with week 6 and week 12 absolute PASI improvement (FIG. 4B). Notably, there was no significant enrichment when using week 0 gene expression profiles in lesional skin. When using percentage PASI improvement as a measure, the same Type I IFN signature enrichment was observed (e.g., week 6 for IFN-α and week 12 for IFN-γ), and enrichment for IL-17A responses was observed at week 12. It is notable that both USP18 and KRT2 were significantly differentially expressed upon TNF stimulation in keratinocytes, and USP18 was up-regulated by IFNs (FIG. 8).

Figure 5A:
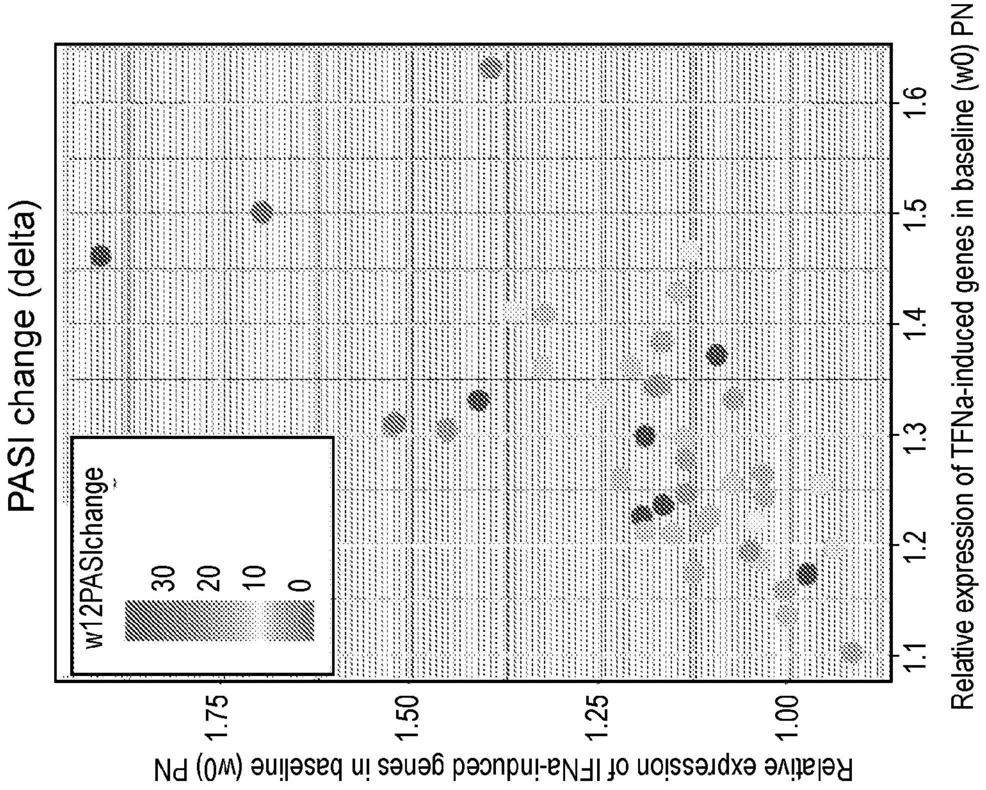
FIG. 5A-D provides an assessment of PASI response in week 12 using baseline uninvolved skin expression profiles.
Figure 5B:
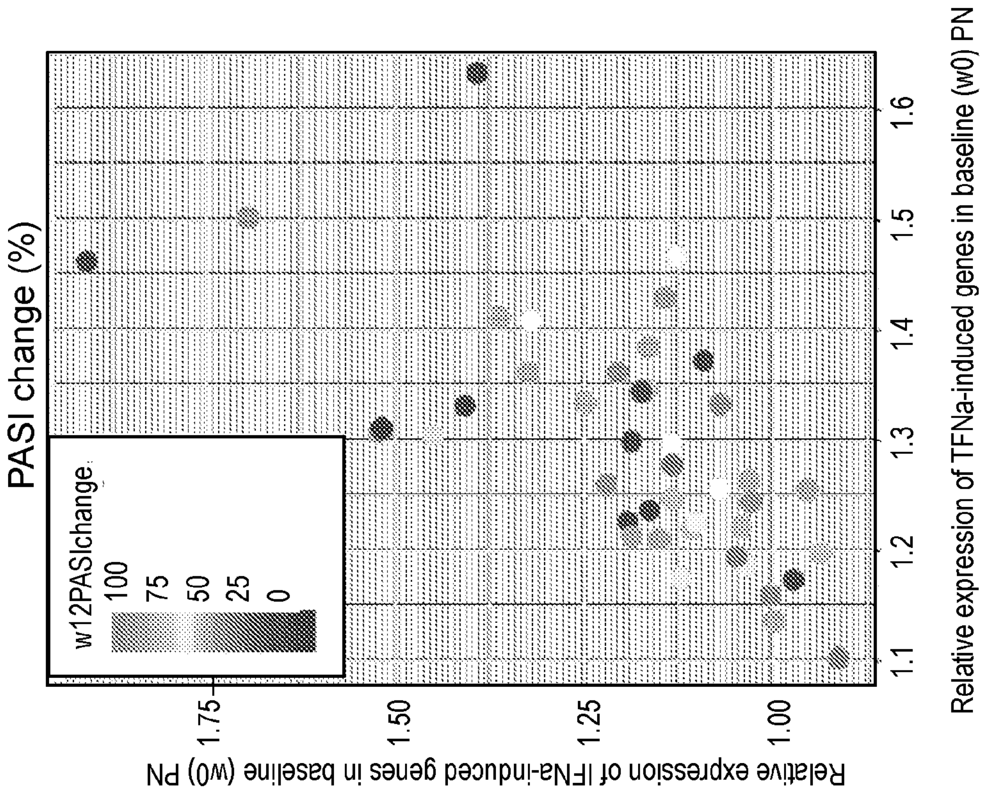

Each patient from the cohort was assigned a TNF or IFN score (see Example 1), summarizing the respective cytokine signature loading for the uninvolved skin of that patient at baseline (FIG. 5A-B). Among the patients showing higher IFN or TNF scores, a higher proportion of PASI improvement was observed in terms of both absolute or percentage measures. It therefore was hypothesized that by using cytokine signatures from keratinocytes as prior information, drug response assessment could be provided. To provide the most robust drug response assessment, a genomic approach was used. Greater than 2,900 genes were identified as being dysregulated upon cytokine stimulation in independent experiments. For each psoriatic patient in the cohort, the principal components of the baseline uninvolved skin expression levels for >2,900 genes that were induced in response to treatment with TNF-α, IFN-α or IFN-γ were obtained.

Figure 5C:
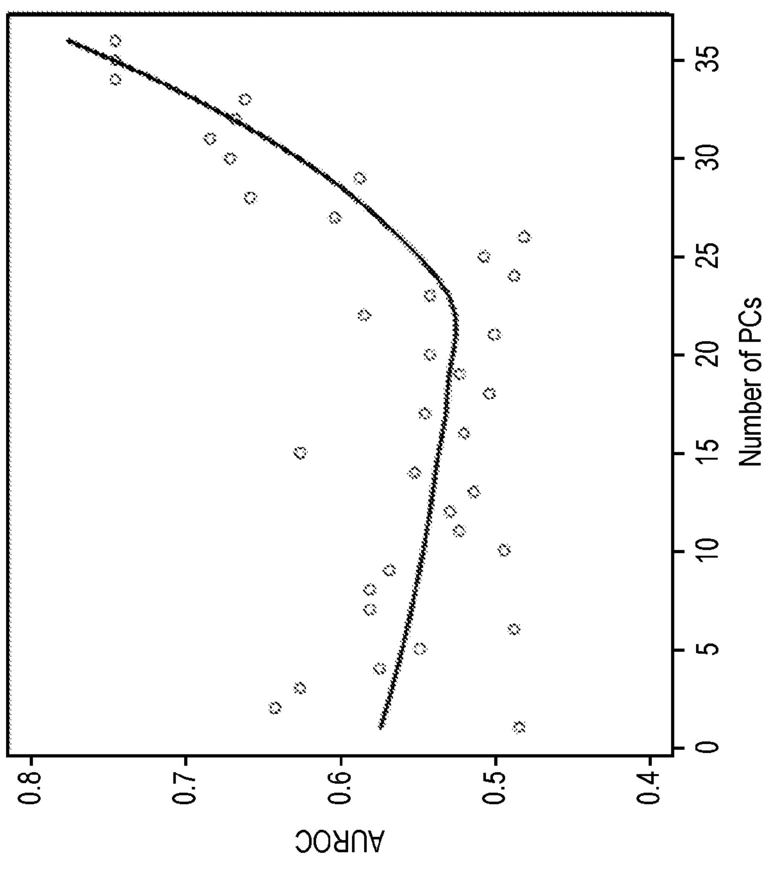
Figure 5D:
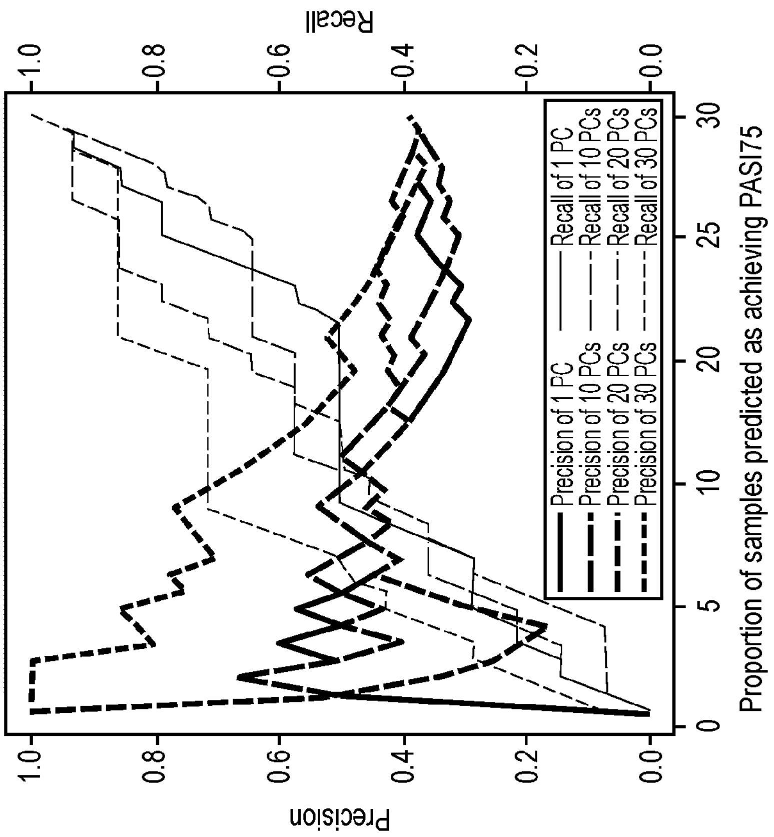

Logistic regression was applied to these components to model the drug responses at week 12 using the PASI 75 criteria, using the leave-one-out validation to ensure robustness upon model evaluation, up to 0.75 in area under the receiver operating characteristic (AUROC) (FIG. 5C) was able to be obtained. To further assess the potential clinical implications, precision (proportion of true positives among the predicted PASI 75) and recall (proportion of actual PASI 75 predicted) were measured as functions of the proportion of top samples predicted from the model (FIG. 5D). Among the top 20% of samples exhibiting the top PASI 75 predicted score, up to 80% accuracy was achieved, representing the ability to use uninvolved skin transcriptome at baseline to identify patients that will most likely benefit from etanercept treatment.

Example 5

Integrative Approach to Identify Additional Genes Important in Assessing Drug Response of Etanercept To identify predictors of treatment outcome with etanercept, a longitudinal study with 210 RNA-seq samples from 46 patients with chronic plaque psoriasis treated with etanercept was conducted.

An integrative approach was taken to identify the most informative biological features that can assess the drug response of etanercept at week 12, combining longitudinal tissue molecular profiling (RNA-seq), and cross compared against RNA-seq data from in vitro independent cytokine-stimulated keratinocytes in conjunction with statistical modeling. The associations between baseline gene expression profiles and clinical presentation were examined. The expression level (from uninvolved skin) of each gene was measured using RNA-seq at week 0, and was correlated with the change in PASI score in each of the three follow-up visits (at weeks 2, 6, and 12). Both percent (%) change as well as absolute (i.e. delta) change in disease improvement, referencing the week 0 values, were evaluated.

Significant associations between gene profiles in baseline uninvolved skin versus PASI improvement from at least one of the follow-up visits were identified only when using percent change as measure. There were 198 genes with their week 0 expression profiles significantly (false discovery rate (FDR)<=10%) associated with week 12 PASI improvement; when using absolute change as measure. There were 192 genes with their baseline expression profiles significantly associated with week 6 12 PASI improvement. There were 391 genes with their baseline expression profiles significantly associated with week 12 PASI improvement.

Among the genes identified to have their baseline expression levels associating with PASI improvement at week 12, 105 of them overlapped between the percent and absolute measures. USP18, an ubiquitin specific peptidase, and KRT2, a type I cytokeratin, are two prominent examples with expression in uninvolved skin at baseline showing significant association with PASI improvement in follow-up visit (FIG. 1). USP18 was significantly up-regulated in lesional skin at baseline (Fold Change (FC)=2.5; $p=1\times10^{-26}$), and its expression in uninvolved skin at baseline was positively correlated with absolute PASI improvement at week 12 ($p=9.8\times10^{-4}$). KRT2 was significantly down-regulated in lesional skin at baseline (FC=0.32; $p=1.3\times10^{-6}$) and its expression in uninvolved skin at week 0 was inversely correlated with both the absolute ($p=1.4\times10^{-5}$) and percent ($p=5.4\times10^{-4}$) PASI improvement at week 12. Although their associations with PASI improvement at weeks 2 and 6 were not significant statistically, the direction of correlations is consistent (FIGS. 1A and 1D). Interestingly, these associations were not observed when using baseline expression levels in lesional skin (FIGS. 1B and 1D). Furthermore, the expression levels of these two genes in lesional skin gradually "restored" toward expression levels in uninvolved skin over time (FIGS. 1C and 1F). These results indicate that both USP18 and KRT2 are dysregulated in psoriatic skin but can be "restored" to uninvolved skin levels by etanercept treatment, and their expression levels in uninvolved skin prior to treatment with etanercept are associated with future PASI improvement.

To model the week 12 PASI response, baseline (week zero) uninvolved skin gene expression profiles for the >2,900 genes induced by cytokine stimulation, e.g., TNF/Type I IFN (as identified by previous keratinocytes experiments), were utilized as described herein above. For each psoriatic patient in the cohort, the principal components of the baseline uninvolved skin expression levels for >2,900 genes that were induced in response to treatment with TNF-α, IFN-α or IFN-γ were obtained.

Logistic regression was applied to model the drug responses at week 12 using the PASI 75 criteria, using leave-one-out to ensure the robustness upon model evaluation (i.e., principal component analysis and regression modeling were performed only on the training data). Area under the receiver operative characteristic (AUROC) for PASI 75 was computed using different number of principal components. To further assess the potential clinical implication, precision (proportion of true positives among the predicted PASI 75) and recall (proportion of actual PASI 75 predicted) were measured as functions of the proportion of top samples predicted from the model. Up to 0.75 in AUROC was obtained (FIG. 2). Among the top 20% of samples exhibiting the top PASI 75 prediction, up to 80% accuracy in predictive response was achieved, representing the ability to use the uninvolved skin transcriptome at baseline to identify patients that will most likely benefit from etanercept treatment.

Regression analysis was applied to identify genes whose expression levels correlated with drug responses in psoriatic patients who will most likely benefit from etanercept treatment. USP18, KRT2, IL4R, SOX5, and IFIH1 were identified as the top protein-coding gene candidates to be used biomarkers for indicating whether a psoriatic patient will favorably respond to treatment with an anti-TNF agent. To evaluate the robustness of this approach, the feature selection process was repeated 36 times, leaving out a different sample each time, and assessing the performance of the left-out samples, achieving AUROC>0.75.

This study showed that by modeling with in vitro genomic data on cytokine responses, significant associations between gene profiles from uninvolved skin at baseline and improvement in psoriasis severity index (PASI) at follow-up visits were identified. Notably, gene profiles in uninvolved, but not inflamed skin, at baseline were the best predictors of treatment response at week 12. These results demonstrate feasibility of assessing drug response in psoriasis utilizing uninvolved skin and implicate involvement of IFN/TNF regulators in anti-TNF responses.

Example 6

Assessing PASI Improvement in Response to Treatment with Etanercept

Each gene expression profile from baseline uninvolved or lesional skin samples was correlated against change in PASI, body surface area (BSA), and static Physician Global Assessment (sPGA) in each of the three follow-up visits. Each sample was adjusted for age, gender, and baseline BMI of the patients, and evaluated both percent (%) as well as absolute (i.e., delta) disease improvement referencing the week 0 (i.e. day 0) values. False Discovery Rate 0% was declared significant for association. Specifically, regression analysis was applied to identify genes whose expression levels correlated with drug responses in psoriatic patients who will most likely benefit from anti-TNF (e.g. etanercept) treatment. USP18, KRT2, IL4R, SOX5, and IFIH1 were identified as the top protein-coding gene candidates to be used also biomarkers for indicating whether a psoriatic patient will favorably respond to treatment with an anti-TNF agent. Age, gender, and BMI were used as covariate in the regression analysis. The p-values for these genes in the association analysis were as follows:

USP18: $9.81\times10^{-4}$;
KRT2: $1.45\times10^{-5}$;
IFIH1: $2.12\times10^{-3}$;
SOX5: $1.85\times10^{-3}$; and
IL4R: $1.6\times10^{-5}$.

Using USP18 as a biomarker for predicting responsiveness to etanercept, a 20% increased level from the baseline or mean level of USP18 in the control (i.e., mean level in uninvolved skin from psoriatic patients prior to treatment) showed an average 2.3 point improvement in PASI in a subject at week 12 of treatment with etanercept. Using KRT2 as a biomarker for predicting responsiveness to etanercept, a 20% increased level from the baseline mean level of KRT2 in the control (i.e., uninvolved skin from psoriatic patients) showed an average 0.99 point improvement in PASI in a subject at week 12 of treatment with etanercept. Using IL4R as a biomarker for predicting responsiveness to etanercept, a 20% increased level from the mean level of IL4R in the control (i.e., uninvolved skin from psoriatic patients) showed an average 5.5 point improvement in PASI in a subject at week 12 of treatment with etanercept. Using SOX5 as a biomarker for predicting responsiveness to etanercept, a 20% increased level from the mean level of SOX5 in the control (i.e., uninvolved skin from psoriatic patients) showed an average 2.3 point improvement in PASI in a subject at week 12 of treatment with etanercept. Using IFIH1 as a biomarker for predicting responsiveness to etanercept, a 20% increased level from the mean level of IFIH1 in the control (i.e., uninvolved skin from psoriatic patients) showed an average 4.1 point improvement in PASI in a subject at week 12 of treatment with etanercept.

The disclosure has been described in terms of particular embodiments found or proposed to comprise specific modes for the practice of the disclosure. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for treating psoriasis in a subject, the method comprising:

measuring a level of at least one biomarker in a biological sample of uninvolved, non-inflamed skin isolated from a subject with psoriasis prior to treatment with an anti-tumor necrosis factor (anti-TNF) agent, wherein the at least one biomarker is (a) ubiquitin specific protease 18 (USP18) and the level of USP18 is increased relative to a control level;

(b) keratin, type II cytoskeletal 2 epidermal (KRT2) and the level of KRT2 is decreased relative to a control level;

(c) interleukin 4 receptor (IL4R) and the level of IL4R is increased relative to a control level;

(d) sex-determining region Y-box transcription factor 5 (SOX5), and the level of SOX5 is decreased relative to a control level; or (e) interferon induced with helicase C domain 1 (IFIH1), and the level of IFIH1 is increased relative to a control level; or (f) a combination of biomarkers of any two or more of (a)-(e), wherein (i) the increased level of USP18, IL4R, or ILH1 or the decreased level of KRT2 or SOX5, or (ii) the increased level of USP18, IL4R, or ILH1 and/or the decreased level of KRT2 or SOX5 in the combination of any two or more biomarkers in the sample of uninvolved, non-inflamed skin isolated from the subject relative to the control level predicts that the subject will be responsive to treatment with the anti-TNF agent, and wherein the control level is the mean level of the biomarker in uninvolved, non-inflamed skin in a population of subjects suffering from psoriasis prior to treatment with the anti-TNF agent; and administering an effective amount of an anti-TNF agent to the subject predicted to be responsive to treatment.

2. The method of claim 1, wherein the at least one biomarker is (a) ubiquitin specific protease 18 (USP18) and the level of USP18 is increased relative to a control level;

(b) keratin, type II cytoskeletal 2 epidermal (KRT2) and the level of KRT2 is decreased relative to a control level;

(c) interleukin 4 receptor (IL4R) and the level of IL4R is increased relative to a control level;

(d) sex-determining region Y-box transcription factor 5 (SOX5), and the level of SOX5 is decreased relative to a control level;

(e) interferon induced with helicase C domain 1 (IFIH1), and the level of IFIH1 is increased relative to a control level.

3. The method of claim 1, wherein the level of USP18 is increased by at least about 86% or more relative to the control level; the level of KRT2 is decreased by at least about 99% or more relative to the control level; the level of IL4R is increased by at least about 36% or more relative to the control level; the level of SOX5 is decreased by at least about 89% or more relative to the control level; or the level of IFIH1 is increased by at least about 49% or more relative to the control level.

4. The method of claim 1, wherein the level is a measure of the level of a nucleic acid or protein present in the biological sample.

5. The method of claim 1, wherein the anti-TNF agent is etanercept, infliximab, adalimumab, certolizumab pegot, or golimumab.

6. The method of claim 1, wherein the anti-TNF agent is thalidomide, lenalidomide, pomalidomide, a xanthine derivative, or bupropion.

7. The method of claim 1, wherein the psoriasis is plaque psoriasis, guttate psoriasis, inverse psoriasis, intertriginous psoriasis, pustular psoriasis, erythrodermic psoriasis, or psoriatic arthritis.

8. The method of claim 1, further comprising administering to the subject at least one additional treatment or medication for psoriasis.

9. The method of claim 1, wherein the subject is a human subject.

10. The method of claim 1, wherein the combination of any two or more of biomarkers comprises USP18 and KRT2.

* * * * *